US 12,070,494 B2
Page 2

(12) United States Patent
Dallmeier et al.

(10) Patent No.: US 12,070,494 B2
(45) Date of Patent: Aug. 27, 2024

(54) CHIMERIC FLAVIVIRUS LYSSAVIRUS VACCINES

(71) Applicant: KATHOLIEKE UNIVERSITEIT LEUVEN, Leuven (BE)

(72) Inventors: Kai Dallmeier, Kessel-Lo (BE); Niraj Mishra, Leuven (BE); Johan Neyts, Kessel-Lo (BE); Lorena Sanchez, Wijgmaal (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 640 days.

(21) Appl. No.: 17/273,985

(22) PCT Filed: Sep. 6, 2019

(86) PCT No.: PCT/EP2019/073897
§ 371 (c)(1),
(2) Date: Mar. 5, 2021

(87) PCT Pub. No.: WO2020/049175
PCT Pub. Date: Mar. 12, 2020

(65) Prior Publication Data
US 2021/0353735 A1 Nov. 18, 2021

(30) Foreign Application Priority Data
Sep. 7, 2018 (GB) ...................... 1814563

(51) Int. Cl.
*A61K 39/12* (2006.01)
*A61K 39/00* (2006.01)
*C12N 7/00* (2006.01)
*C12N 15/85* (2006.01)

(52) U.S. Cl.
CPC ............... *A61K 39/12* (2013.01); *C12N 7/00* (2013.01); *C12N 15/85* (2013.01); *A61K 2039/5254* (2013.01); *C12N 2760/20134* (2013.01); *C12N 2770/24134* (2013.01); *C12N 2800/204* (2013.01); *C12N 2820/002* (2013.01)

(58) Field of Classification Search
CPC ............ A61K 39/12; A61K 2039/5254; C12N 7/00; C12N 15/85; C12N 2760/20134; C12N 2770/24134; C12N 2800/204; C12N 2820/002; C12N 2770/24161; Y02A 50/30; A61P 31/14; C07K 14/005

See application file for complete search history.

(56) References Cited

U.S. PATENT DOCUMENTS

| 4,393,201 A * | 7/1983 | Curtis ................ C07K 14/005 |
| | | 435/69.3 |
| 2008/0268423 A1* | 10/2008 | Barrett ............. G01N 33/56983 |
| | | 435/235.1 |
| 2010/0297167 A1* | 11/2010 | Bonaldo ................ A61K 39/12 |
| | | 435/235.1 |
| 2013/0243812 A1* | 9/2013 | Pugachev ............. A61K 39/205 |
| | | 435/235.1 |

FOREIGN PATENT DOCUMENTS

| WO | 2005042014 A1 | 5/2005 | |
| WO | 2008100464 A1 | 8/2008 | |
| WO | WO-2008100464 A1 * | 8/2008 | ............. A61K 39/12 |
| WO | 2014174078 A1 | 10/2014 | |
| WO | 2018027290 A1 | 2/2018 | |

OTHER PUBLICATIONS

Written Opinion mailed Nov. 29, 2019 in reference to co-pending European Patent Application No. PCT/EP2019/073897 filed Sep. 6, 2019.
International Search Report mailed Nov. 29, 2019 in reference to co-pending European Patent Application No. PCT/EP2019/073897 filed Sep. 6, 2019.
Xiaohong Jiang et al., "Yellow fever 17D-vectored vaccines expressing Lassa virus GP1 and GP2 glycoproteins provide protection against fatal disease in guinea pigs", Vaccine, Elsevier, Amsterdam, NL, vol. 29, No. 6, pp. 1248-1257, Nov. 24, 2010, XP028175836.
Natalia A Kuzmina et al., "Conservation of Binding Epitopes for monoclonal antibodies on the Rabies Virus Glycoprotein", Journal of Antivirals and Antiretrovirals, vol. 5, No. 2, Jan. 1, 2013, XP055647036.
Almazan et al., "Engineering the largest RNA virus genome as an infectious bacterial artificial chromosome", Proceedings of the National Academy of Sciences of the United States of America, vol. 97, No. 10, pp. 5516-5521, May 9, 2000, XP002166823.
Bredenbeek PJ, et al., "A recombinant Yellow Fever 17D vaccine expressing Lassa virus glycoproteins", Virology, Elsevier, Amsterdam, NL, vol. 345, No. 2, pp. 299-304, Feb. 20, 2006, XP024896770.
Giel-Moloney Maryann, et al., "A novel approach to a rabies vaccine based on a recombinant single-cycle falvivirus vector", Vaccine, vol. 35, No. 49, pp. 6898-6904, Sep. 9, 2017, XP085293351.
Weniger, et al., "ALternative vaccine delivery methods", Section 3, pp. 1200-1231, 2013.
Bonaldo, et al., "The yellow fever 17D virus as a platform for new live attenuated vaccines", Human Vaccines & Immunotherapeutics, vol. 10, No. 5, pp. 1256-1265, May 2014.
Cicin-Sain, et al., "Vaccination of Mice with Bacteria Carrying a Cloned Herpesvirus Genome Reconstituted In Vivo", Journal of Virology, vol. 77, No. 15, pp. 8249-8255, Aug. 2003.
Darji, et al., "Oral delivery of DNA vaccines using attenuated *Salmonella typhimurium* as carrier", FEMS Immunology and Medical Microbiology, vol. 27, pp. 341-349, 2000.

(Continued)

*Primary Examiner* — Rachel B Gill
(74) *Attorney, Agent, or Firm* — Dinsmore & Shohl LLP

(57) ABSTRACT

The invention describes chimeric Flavivirus constructs comprising lyssavirus G proteins in the E/NS1 intergenic region.

Figure 11:
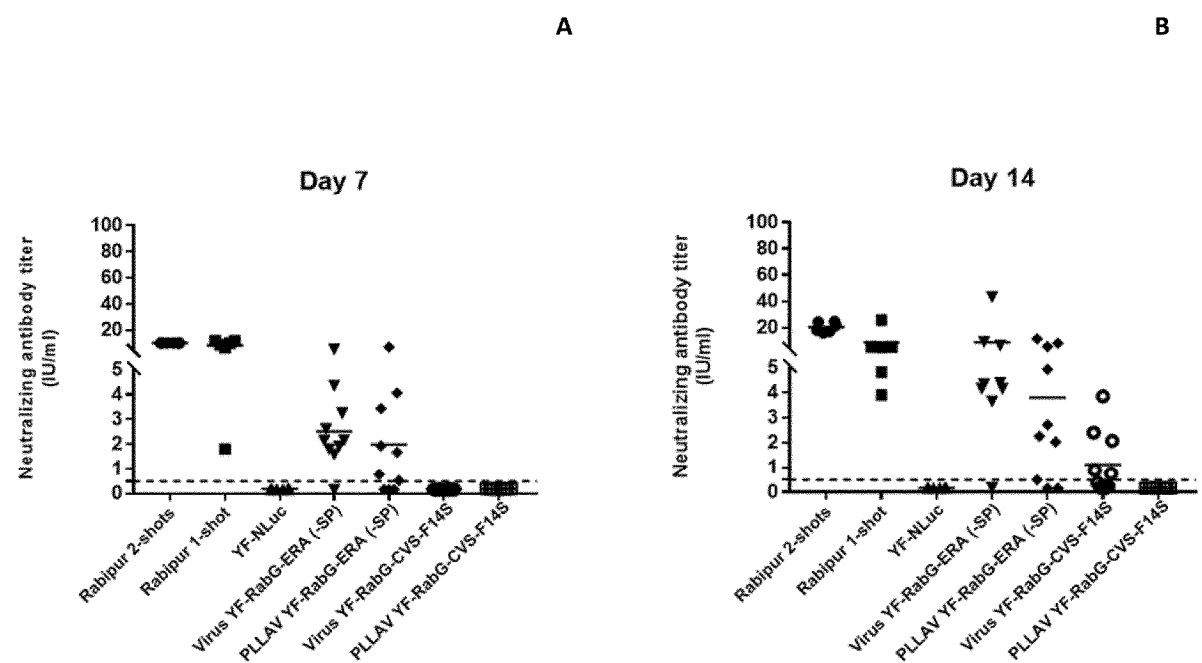

23 Claims, 17 Drawing Sheets
Specification includes a Sequence Listing.

(56) References Cited

OTHER PUBLICATIONS

Muller, et al., "The flavivirus NS1 protein: Molecular and structural biology, immunology, role in pathogenesis and applications as a diagnostic biomarker", Antiviral Research, vol. 98, pp. 192-208, 2013.
Nielsen, et al., "Identification of prokaryotic and eukaryotic signal peptides and prediction of their cleavage sites", Short Communication, Protein Engineering, vol. 10, No. 1, pp. 1-6, 1997.
Nowak, et al., "Analyses of the Terminal Sequences of West Nile Virus Structural Proteins and of the in Vitro Translation of these Proteins Allow the Proposal of a Complete Scheme of the Proteolytic Cleavages Involved in Their Synthesis", Virology, vol. 169, pp. 365-376, 1989.
Op De Beeck, et al., "Role of the Transmembrane Domains of prM and E Proteins in the Formation of Yellow Fever Virus Envelope", Journal of Virology, vol. 77, No. 2, pp. 813-820, Jan. 2003.
Op De Beeck, et al., "The Transmembrane Domains of prM and E Proteins of Yellow Fever Virus Are Endoplasmic Reticulum Localization Signals", Journal of Virology, vol. 78, No. 22, pp. 12591-12602, Nov. 2004.
Préhaud, et al., "Glycoprotein of Nanopathogenic Rabies Viruses Is a Key Determinant of Human Cell Apoptosis", Journal of Virology, vol. 77, No. 19, pp. 10537-10547, Oct. 2003.
Babiuk, et al., "Delivery of DNA Vaccines Using Electroporation", Methods in Molecular Medicine, Second Edition, vol. 127, pp. 73-136, 2011.
Translation of Office Action pertaining to related Japanese Patent Application No. 2021-512782.
Youn, Soonjeon et al., Journal of Virology. Sep. 2010. "A Short N-Terminal Peptide Motif on Flavivirus Nonstructural Protein NS1 Modulates Cellular Targeting and Immune Recognition".

\* cited by examiner

A

[Diagram: YF-E | TM 1 | TM 2 | SP | RabG | TM | TM WNV | YF-NS1; with 9 aa NS1 marker and RabG_ERA boxed region]

B

YF17D | RabG (E/NS1)

Plaques stained at 6dpi. BHK-21J cells

C

IP: $10^5$ TCID$_{50}$ YFV-RabG(E/NS1)
or
IP: 25 μg plasmid + PEI

AG129 mice (n= 3 each)

Day 14: 1. bleeding 2. boosted
Day 28: 1. bleeding 2. boosted
Day 42: termination

| Condition | survival | Day 14 | | Day 28 | | Day 42 | |
|---|---|---|---|---|---|---|---|
| | | Anti-YFV IgG | Anti-RABV nAb | Anti-YFV IgG | Anti-RABV nAb | Anti-YFV IgG | Anti-RABV nAb |
| IP: YFV 17D-RabG(E/NS1) | 3/3 | 2/3 | 1/3 | 3/3 | 3/3 | n.d | 2/3 |
| IP: YFV 17D-RabG(E/NS1)-PLLAV+PEI | 3/3 | 0/3 | 0/3 | 0/3 | 0/3 | n.d. | 0/3 |

Figure 1

A

YF17D

ERA-RabG (Clone 9)

D82-ERA-RabG #1

D82-ERA-RabG #2

D82-ERA-RabG #9

D82-ERA-RabG #12

B

| Constructs insertion in YF E/NS1 D82 | |
|---|---|
| pSYF17D-D82-ERA-RabG-ENS1 #1 | 3 mutations in RabG<br>1 mutation in TM-WNV |
| pSYF17D-D82-ERA-RabG-ENS1 #2 | 1 mutation in RabG<br>1 mutation in YF-E TM-1 |
| pSYF17D-D82-ERA-RabG-ENS1 #9 | 1 mutation in YF-E TM-2 |
| pSYF17D-D82-ERA-RabG-ENS1 #12 | No mutation |

YF-E | TM 1 | TM 2 | 9 aa NS1 ↓ SP | RabG | TM | TM WNV | YF-NS1

RabG$_{CVS}$

B

YF17D          YF17D-CVS-RabG

Figure 4

A

YF17D-coCVS
Virus 4dpt or purified
from plaque 1    1. bleeding
                            2. boosted      bleeding            termination AG129 mice         Day 14           Day 28           Day 42
(n= 3 each)

B

| Condition | survival | Day 14 | | Day 28 | |
|---|---|---|---|---|---|
| | | Anti-YFV IgG | Anti-RABV nAb | Anti-YFV IgG | Anti-RABV nAb |
| IP: YFV 17D-coCVS-RabG 4dpt | 2/3 M914 M916 M919 (dead) | 2/3 | 2/3 M914   1.33 IU/ml M916   0.44 IU/ml | 2/3 | 2/3 M914   2.79 IU/ml M916   4 IU/ml |
| IP: YFV 17D-coCVS-RabG Plaque purified (mutation F14S) | 3/3 M915 M917 M918 | 3/3 | 2/3 M915   0.25 IU/ml M917   2.24 IU/ml M918   3.28 IU/ml | 3/3 | 3/3 M915   0.54 IU/ml M917   11.45 IU/ml M918   8.12 IU/ml |

YFV17D
1.2x10⁵ pfu/ml

YFV17D-ERA(-SP) RabG
3.1 x 10⁴ pfu/ml

B

αRabG　　αYF　　Merge　　Merge (DAPI)

Figure 7

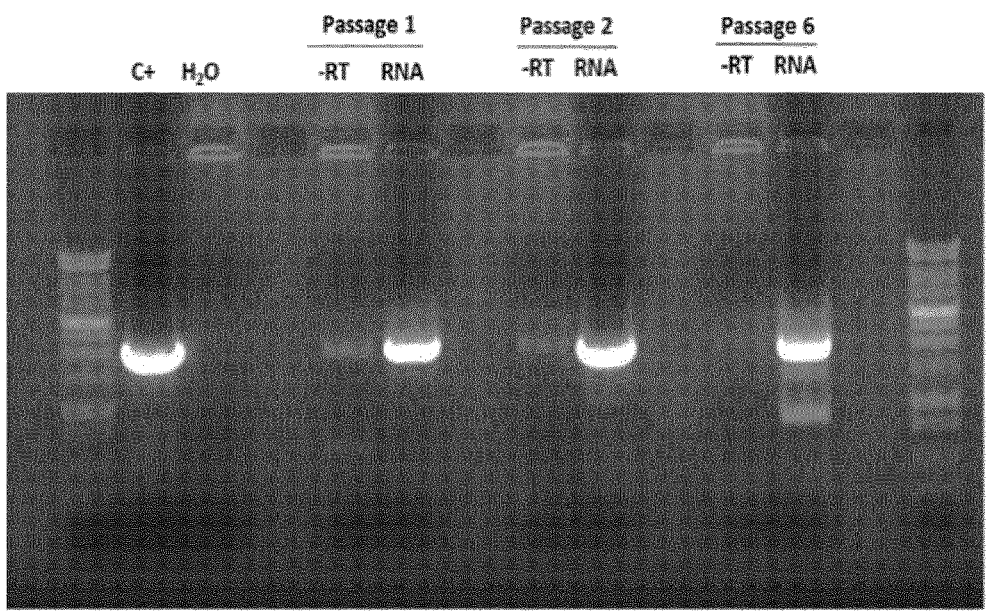
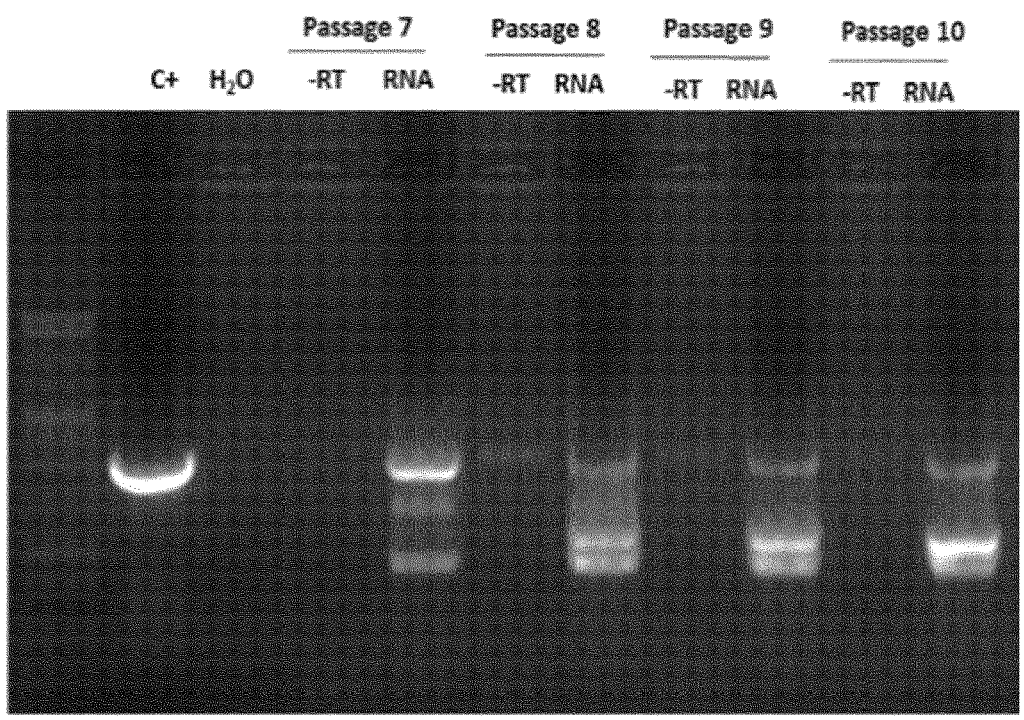
Figure 8

YF17D-coERA(-SP)
Virus 4dpt

AG129 mice (n= 5 each) | Day 14: 1. bleeding 2. boosted | Day 28: 1. bleeding 2. boosted | Day 42: 1. bleeding 2. termination

A

YF17D-ERA(-SP)-RabG (E/NS1)

B

Neutralizing antibodies titer (IU/ml) plotted at day 14, day 28, day 42

Figure 9

AG129 mice timeline: Day -7, Day 0, Day 7, Day 14, Day 21, Day 28

| | #animals | day -7 | day 0 | day 7 | day 14 | day 21 | day 28 |
|---|---|---|---|---|---|---|---|
| Rabipur 2 shots (1/10 human dose) | 6 | 1 vaccination | Boosting | | | | |
| Rabipur 1 shot (1/10 human dose) | 6 | | 1 vaccination | | | | |
| YF17D-NLuc virus (60000 PFU) | 6 | | 1 vaccination | | | | |
| YF17D-RabG$_{ERA}$(DSP) virus (7750 PFU) | 10 | | 1 vaccination | Bleeding | Bleeding | Bleeding | Bleeding |
| PLLAV-YF17D-RabG$_{ERA}$(DSP) (25 ug+ PEI) | 10 | | 1 vaccination | | | | |
| YF17D-CVS-F14S plaque purified (750 PFU) | 10 | | 1 vaccination | | | | |
| PLLAV-YF17D-CVS-F14S (25 ug+ PEI) | 10 | | 1 vaccination | | | | |

Virus (IP)
ChimeriVaxZIKV-RabG
200 PFU

AG129 mice
(n= 5)

Day 17 — bleeding
Day 28 — bleeding
Day 42 — termination

B

| Condition | Survival | Day 17 | | | Day 28 | | |
|---|---|---|---|---|---|---|---|
| | | Anti-ZIKV IgG | Anti-YFV IgG | Anti-RABV nAb | Anti-ZIKV IgG | Anti-YFV IgG | Anti-RABV nAb |
| IP: ChimeriVaxZIKV-RabG (virus) | 5/5 | 5/5 | 5/5 | 5/5 | 5/5 | 5/5 | 4/5 |

C1 — [1] C | [2] prME | [3] RabG | [1] NS1-5 — YF17D-RabG (phylogroup I)

C2 — C | prME | LBV-G | NS1-5 — YF17D-LBV-G (phylogroup II)

C3 — C | prME | MOKV-G | NS1-5 — YF17D-MOKV-G (phylogroup II)

C4 — C | prME | LLEBV-G | NS1-5 — YF17D-LLEBV-G (phylogroup III)

(D)

D1 — [1] C | [2] prME | [3] RabG | [1] NS1-5 — JE SA14-14-2-RabG

Figure 16 (continued)

CHIMERIC FLAVIVIRUS LYSSAVIRUS VACCINES

CROSS-REFERENCES TO RELATED APPLICATIONS

This application is a national-stage application under 35 U.S.C. § 371 of International Application PCT/EP2019/073897, filed Sep. 6, 2019, which international application claims the benefit of priority to Great Britain Patent Application No. 1814563.1, filed Sep. 7, 2018.

REFERENCE TO SEQUENCE LISTING SUBMITTED ELECTRONICALLY

The instant application contains a Sequence Listing that has been submitted electronically in ASCII format and is hereby incorporated by reference in its entirety. The ASCII copy, created Mar. 5, 2021, is named "KAT0053PA_Sequence_ST25.txt" and is 27 KB in size.

Field of the invention

The invention relates to chimeric Flavivirus based vaccines. The invention further relates to vaccines against rabies.

BACKGROUND OF THE INVENTION

Rabies vaccines for use in humans are purified cell culture and embryonated egg-based rabies vaccines (CCEEVs) that contain inactivated rabies virus (RABV). These vaccines are inactivated viral vaccines that require a multiple-dose regimen, a cold chain and high costs to produce and maintain them. These vaccines fail to prevent human rabies in the main target group which are people in endemic areas. Furthermore, the immunoprotection induced by prophylactic vaccination wanes relatively rapidly which involves the requirement of post-exposure treatment with combination of immunoglobulins (RIG) and a vaccine regimen.

Rabies glycoprotein G (RabG) which is responsible for cell attachment and membrane fusion, and is a key immunogen targeted for vaccine development. Rabies Glycoprotein G and its epitopes are reviewed in Kuzmina et al. (2013) *J antivir antiretrovir.* 5:2 37-43.

Bonaldo et al. (2014) *Human Vacc. & Immunother.* 10, 1256-1265 review the Yellow Fever virus (YFV) chimeric constructs wherein non-Flavivirus antigens are inserted in the YFV genome.

An approach involving the replication-defective vaccine platform RepliVax™ (RV) West Nile virus (WNV) has been used to obtain a rabies vaccine (RV-RabG) (Giel-Moloney et al. (2017) Vaccine. 35(49 PtB), 6898-6904). In this approach several RV-RabG constructs were generated by inserting the Rabies virus Glycoprotein G gene in different WN deletion variants (C, prME or CprME WN genes were exchanged with the RabG gene). A full-length RabG protein was used including the native RabG signal sequence with a 2A self-cleavage element at the C-terminus.

These constructs require to be in vitro-transcribed and transfected in baby hamster kidney (BHK) helper cells (HC) expressing structural WN C-prM-E proteins required for packaging the RV-RabG replicons as single-component pseudo infectious viruses (sPIVs) that are used as vaccine. These PIVs induce specific antibodies response against rabies and WN.

Yellow fever virus 17D has been used as a vector for Lassa virus glycoprotein (GPC) or its subunits GP1 and GP2 (Bredenbeek et al. (2006) *Virology* 345, 299-304 and Jiang et al. (2011) Vaccine. 29, 1248-1257). In these constructs the GP gene (lack of signal peptide, SSP) (or either GP1 or GP2 sequences) were inserted between YF-E/NS1. These constructs have at the C-terminus of the insert fusion sequences derived from YF-E (23 C terminal hydrophobic amino acids of YF-E), WNV-E or artificial designed sequences. These constructs need to be transfected in cells and the viruses derived from them are used as vaccines.

The RepliVax™-RabG (RV-RabG) constructs cannot be used directly as vaccines, it is required to generate first pseudo-infectious viruses (PIVs) in BHK helper cells (HC) that supply the proteins deleted from the WNV backbone in trans to obtain the PIVs used to vaccinate. This involves high costs of production as well as requires a cold chain to preserve the PIVs.

Regarding the use of YFV17D as vector to express a glycoprotein precursor the main problem with this recombinant virus is the instability that did not allow to scale-up the technology as required for vaccine production.

SUMMARY OF THE INVENTION

The invention describes chimeric Flavivirus constructs comprising lyssavirus G proteins in the E/NS1 intergenic region.

A novel Yellow Fever virus based transgenic vaccine was engineered by inserting RabG into the yellow fever E/NS1 intergenic region of YFV-17D as follows: the N-terminal (Nt) signal peptide of RabG was deleted, the first 9 amino acids of NS1 (27 nucleotides) were added N-terminally of RabG to allow proper release of RabG protein, the RabG cytoplasmic C terminal sequence was preserved and fused to the WNV (West Nile Virus) transmembrane domain 2. The resulting Rabies/YFV-17D construct launches viable live-attenuated viruses expressing functional RabG and YFV-17D proteins. A bacterial artificial chromosome comprising such YFV17D-RabG construct can be used directly as vaccine, indicating that such a DNA-based modality of the YFV17D-RabG construct can be used as thermostable vaccine. The vaccine induces an immune response against both RABV and YFV after one-single shot. YFV17D-RabG is a dual vaccine inducing YFV and rabies virus specific immunity. The BAC comprising YFV17D-RabG can also be used for the production of tissue culture-derived live-attenuated vaccine.

The invention is summarised in the following statements:

1. A polynucleotide comprising a sequence of a live, infectious, attenuated Flavivirus wherein a nucleotide sequence encoding at least a part of a Lyssavirus G protein is inserted/locate at the intergenic region between the E and NS1 gene of said Flavivirus, such that a chimeric virus is expressed, characterised in that the encoded sequence C terminally of the E protein of said Flavivirus and N terminally of the signal peptide of the NS1 protein of said Flavivirus comprises in the following order:
    a further signal peptide of a Flavivirus NS1 protein,
    a lyssavirus G protein comprising a defective functional signal peptide or lacking a functional signal peptide, comprising the IIb epitope, comprising the C terminal TM membrane and comprising the C terminal cytoplasmatic sequence, and
    a TM2 domain of a flaviviral E protein.

2. The polynucleotide according to statement 1, wherein the sequence of the live, infectious, attenuated Flavivirus is Yellow Fever virus, typically the YF17D strain.

3. The polynucleotide according to statement 2, wherein the Flavivirus backbone is a chimeric virus.

4. The polynucleotide according to any one of statements 1 to 3, wherein the Lyssavirus is Rabies virus.

5. The polynucleotide according to any one of statements 1 to 4, wherein the Rabies G protein is of the ERA strain.

6. The polynucleotide according to any one of statements 1 to 5, wherein the nucleotide sequence of the G protein is codon optimised for improved expression in mammalian cells.

7. The polynucleotide according to any one of statements 1 to 6, wherein the further signal peptide of the NS1 protein of the live, infectious, attenuated Flavivirus, comprises or consists of the sequence DQGCAINFG [SEQ ID NO:6].

8. The polynucleotide according to any one of statements 1 to 6, wherein the signal peptide of the NS1 protein, located c terminally of the TM2 domain comprises or consists of the sequence DQGCAINFG [SEQ ID NO:6].

9. The polynucleotide according to any one of statements 1 to 8, wherein the IIb epitope has the sequence GCTNLSGFS [SEQ ID NO:15].

10. The polynucleotide according to any one of statements 1 to 9, wherein the TM2 domain of a flaviviral E protein is from West Nile virus.

11. The polynucleotide according to any one of statements 1 to 10, wherein the TM2 domain of a flaviviral E protein has the sequence RSIAMTFLAVGGVLLFLSVNVHA [SEQ ID NO 13].

12. The polynucleotide according to any one of statements 1 to 11, wherein the defective functional signal peptide of Rab G is a F145 mutation.

13. The polynucleotide according to any one of statements 1 to 12, wherein the Rab G lacks the N terminal signal sequence of amino acids 1 to 19 MVPQALLFVPLL-VFPLCFG [SEQ ID NO 18].

14. The polynucleotide according to any one of statements 1 to 13, wherein the sequence of the chimeric virus comprises at the junction of Flavivirus E gene, NS1 signal peptide and Rab G protein the sequence LGVGA DQGCAINFG KFPIY [SEQ ID NO:21]

15. The polynucleotide according to any one of statements 1 to 14, wherein the sequence of the chimeric virus comprises at the junction of the WNV TM2 domain and the YFV protein the sequence VNVHA DQGCAINFG KRELK [SEQ ID NO: 22].

16. The polynucleotide according to any one of statements 1 to 15, wherein the encoded sequence of the chimeric virus comprises the sequence of SEQ ID NO:2 or a sequence having 95, or 99% sequence identity, or the polynucleotide according to any one of statements 1 to 15, wherein the polynucleotide comprises the sequence of SEQ ID NO:1 or a sequence having 95, or 99% sequence identity therewith.

17. The polynucleotide according to any one of the statements 1 to 16, which is a bacterial artificial chromosome.

18. A polynucleotide in accordance to any one of statement 1 to 17, for use as a medicament.

19. The polynucleotide for use as a medicament in accordance with statement 18, wherein the medicament is a vaccine.

20. A polynucleotide sequence in accordance to any one of statement 1 to 19, for use in the vaccination against a lyssavirus.

21. A chimeric live, infectious, attenuated Flavivirus wherein at least a part of a lyssavirus G protein, such as Rabies G protein is located between the E and NS1 protein of said Flavivirus, such that C terminally of the E protein and N terminally of the signal peptide of the NS1 protein the virus comprises in the following order:
 a further signal peptide of a Flavivirus NS1 protein,
 a lyssavirus G protein comprising a defective functional signal peptide or lacking a functional signal peptide, and comprising the IIb epitope, comprising the C terminal TM membrane and the C terminal cytoplasmatic sequence, and
 a TM2 domain of a flaviviral E protein.

22. A chimeric virus in accordance to statement 21, for use as a medicament.

23. A chimeric virus in accordance to statement 22, for use in the prevention of a lyssavirus.

24. A chimeric virus encoded by a nucleotide in accordance to statement 23, for use in the prevention of a lyssavirus and in the prevention of the Flavivirus.

25. A method of preparing a vaccine against a lyssavirus infection such as Rabies, comprising the steps of:
 a) providing a BAC which comprises
 an inducible bacterial ori sequence for amplification of said BAC to more than 10 copies per bacterial cell, and
 a viral expression cassette comprising a cDNA of a Flavivirus lyssavirus chimeric virus according to any one of statements 1 to 15, and comprising cis-regulatory elements for transcription of said viral cDNA in mammalian cells and for processing of the transcribed RNA into infectious RNA virus
 b) transfecting mammalian cells with the BAC of step a) and passaging the infected cells
 c) validating replicated virus of the transfected cells of step b) for virulence and the capacity of generating antibodies and inducing protection against lyssavirus infection.
 d) cloning the virus validated in step c into a vector
 e) formulating the vector into a vaccine formulation.

26. The method according to statement 25, wherein the vector is BAC, which comprises
 an inducible bacterial ori sequence for amplification of said BAC to more than 10 copies per bacterial cell.

This project has received funding from the European Union's Horizon 2020 research and innovation programme under RABYD-VAX grant agreement No 733176.

DETAILED DESCRIPTION

FIG. 1. A) Schematic representation of YFV17D-RabG-ERA (E/NS1). SP: signal peptide; TM: transmembrane domain. B) Plaque phenotype YFV17D-RabG-ERA (E/NS1) compared to YFV17D. C) Vaccination schedule to test the immunogenicity of YFV17D-RabG-ERA (E/NS1) in AG129 mice. Mortality and serological response to YFV17D-RabG-ERA(E/NS1) in AG129 mice (table) (IP—intraperitoneal; $TCID_{50}$—median tissue culture infectious dose; PEI—polyethylenimine).

FIG. 2: A) Plaque phenotype of BAC progeny expressing ERA-RabG or Δ82-ERA-RabG inserted at YF-E/NS1 site. B) legend to constructs depicted in panel A.

Figure 3:
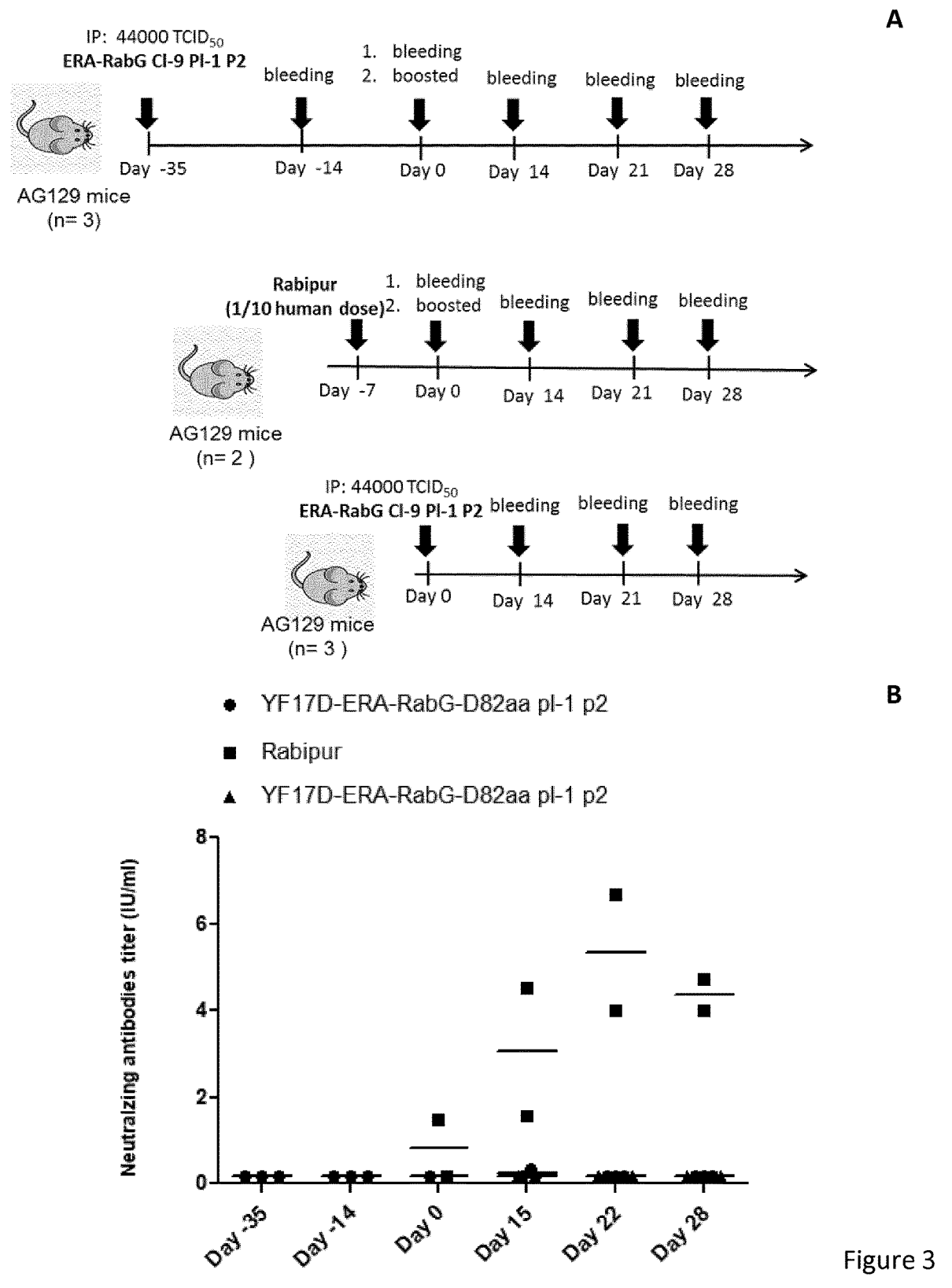

FIG. 3: A) Vaccination schedule to test the immunogenicity of YFV17D-RabG-ERA-Δ82 and Rabipur in AG129 mice. (IP—intraperitoneal; $TCID_{50}$—median tissue culture infectious dose). B) Neutralizing antibody titer against RABV.

FIG. 4: A) Schematic representation of YFV17D-RabG-CVS (E/NS1). SP: signal peptide; TM: transmembrane domain. B) Plaque phenotype YFV17D-RabG-CVS (E/NS1) compared to YFV17D.

FIG. 5: A) Vaccination schedule to test the immunogenicity of YFV17D-RabG-CVS (E/NS1) in AG129 mice. B) Mortality and serological response to YFV17D-RabG-CVS (E/NS1) in AG129 mice (IP—intraperitoneal).

Figure 6:
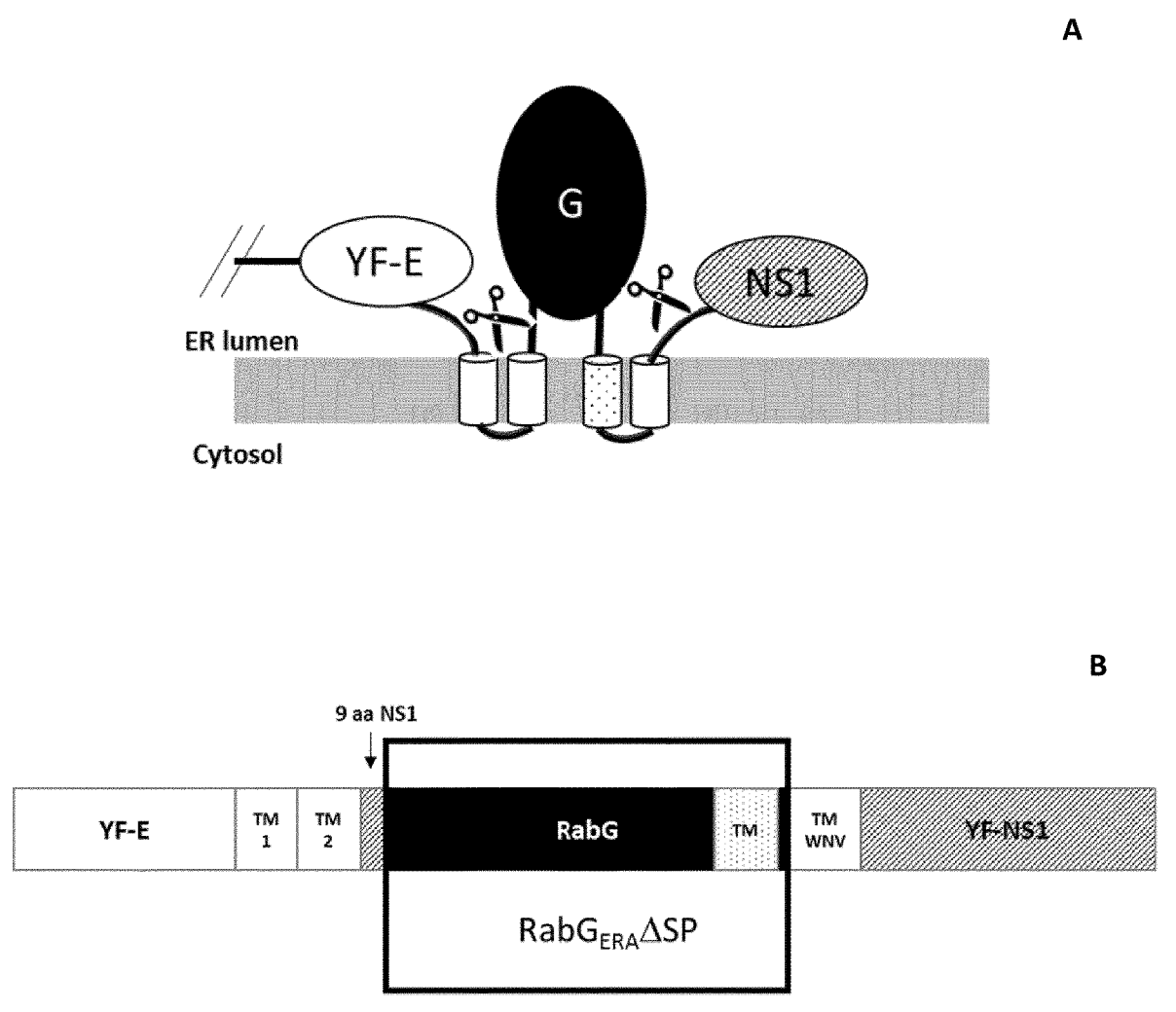

FIG. 6. A) RabG-ERA was inserted between YF-E/NS1 as follows: the N-terminal RabG signal peptide (SP) was removed to accommodate RabG in the YF polyprotein, first 9 aa of NS1 were added at the Nt of Rab G to allow proper release of RabG, the RabG cytoplasmic domain at the C terminus was preserved and fused to the transmembrane domain anchor-2 of WNV to fit RabG in the YF polyprotein topology. B) Schematic representation of YFV17D-RabG$_{ERA}$ΔSP construct.

FIG. 7: A) Plaque phenotype of BAC progeny expressing RabG$_{ERA}$ΔSP. B) Co-expression of RabG$_{ERA}$ΔSP and YFV antigens detected by immunofluorescence of BHK21J cells infected with supernatant of cells transfected with pShuttle-YF17D-RabG$_{ERA}$ΔSP.Cells were fixed 48hp.i. and stained for RabG and YFV.

FIG. 8. RT-PCR analysis of the virus samples harvested during serial passaging of the YF17D-RabG$_{ERA}$ΔSP virus. C+, control positive pSYF17D-YF17D-RabG$_{ERA}$ΔSP; -RT: RT-PCR reaction without retrotranscriptase; RNA: RT-PCR reaction with the virus RNA. (Panel A: passages 1-6; Panel B: passages 7-10)

FIG. 9: A Vaccination schedule to test the immunogenicity of YF17D-RabG$_{ERA}$ΔSP virus in AG129 mice. B) Serum neutralizing antibody (SNA) titer against rabies.

FIG. 10: Single vaccination schedule to test the in vivo immunogenicity of (i) PLLAV-YF17D-RabG$_{ERA}$ΔSP, (ii) YF17D-RabG$_{ERA}$ΔSP virus, (iii) BAC comprising YF17D-CVS-RabG-F14S and (iv) YF17D-CVS-RabG-F14S virus in AG129 mice. YFV-17D-NLuc and Rabipur (single or double vaccination) were used as positive controls for YF and rabies vaccinations respectively.

FIG. 11: Serum neutralizing antibody (SNA) titer against RABV post (A) day 07, (B) day 14, (C) day 21 and (D) day 28 after IP vaccination with (i) PLLAV-YF17D-RabG$_{ERA}$ΔSP, (ii) YF17D-RabG$_{ERA}$ΔSP virus, (iii) BAC with YF17D-CVS-RabG-F14S, (iv) YF17D-CVS-RabG-F14S, (v) YFV-17D-Nluc and (vi) single and (vii) double immunization with Raipur in AG129 mice. Rabipur 2-shots: data correspond with day 7, 14, 21 and 28 after mice were boosted with Rabipur.

Figure 12:
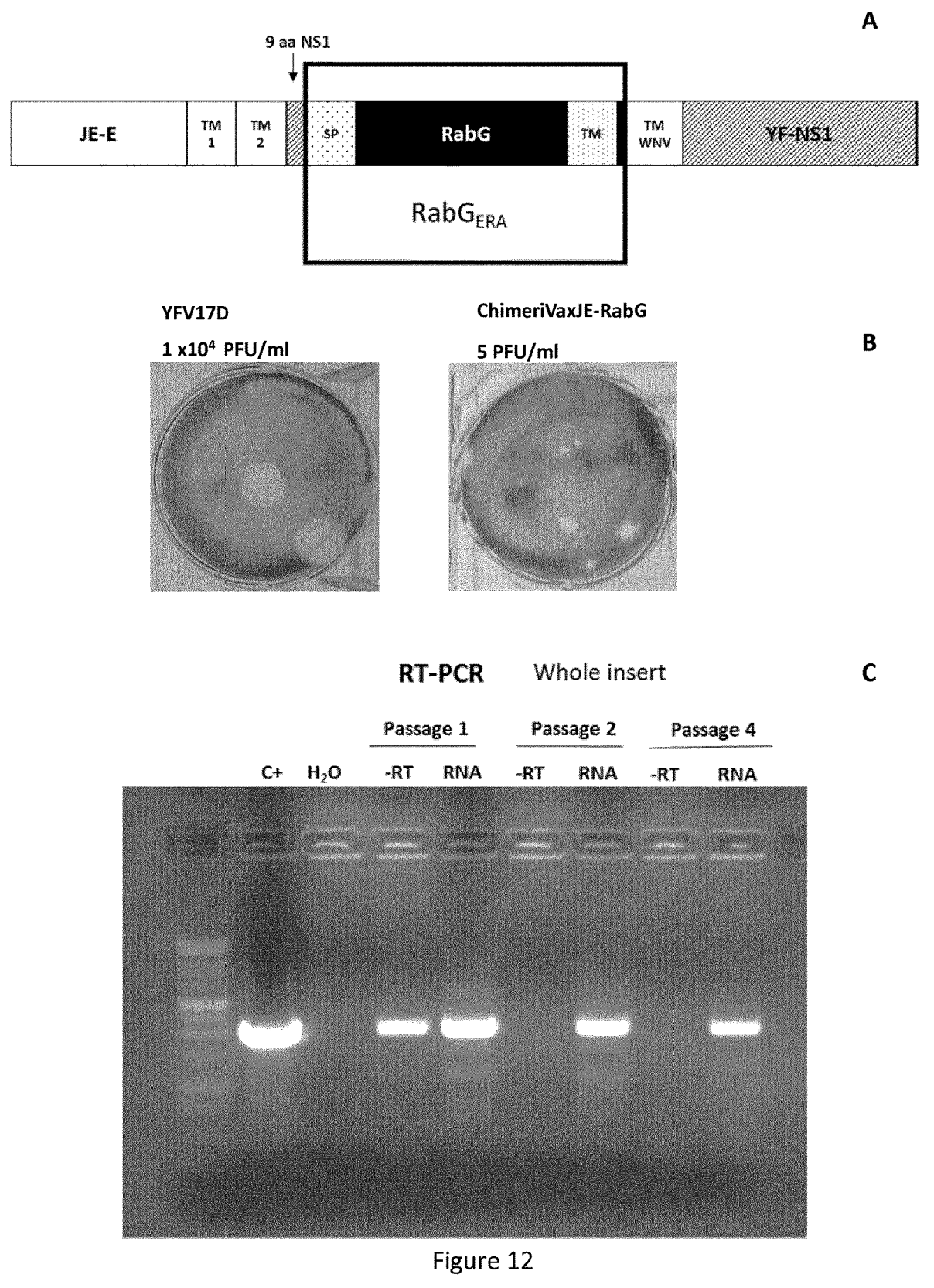

FIG. 12: A) Schematic representation of RabG inserted between JE-E and YF-NS1 (ChimeriVax JE backbone). B) Plaque phenotype ChimeriVaxJE-RabG compared to YF17D. C). RT-PCR analysis of the virus samples harvested during serial passaging of the ChimeriVaxJE-RabG virus. C+, control positive pShuttle-ChimeriVaxJE-RabG; -RT: RT-PCR reaction without retrotranscriptase; RNA: RT-PCR reaction with the virus RNA.

Figure 13:
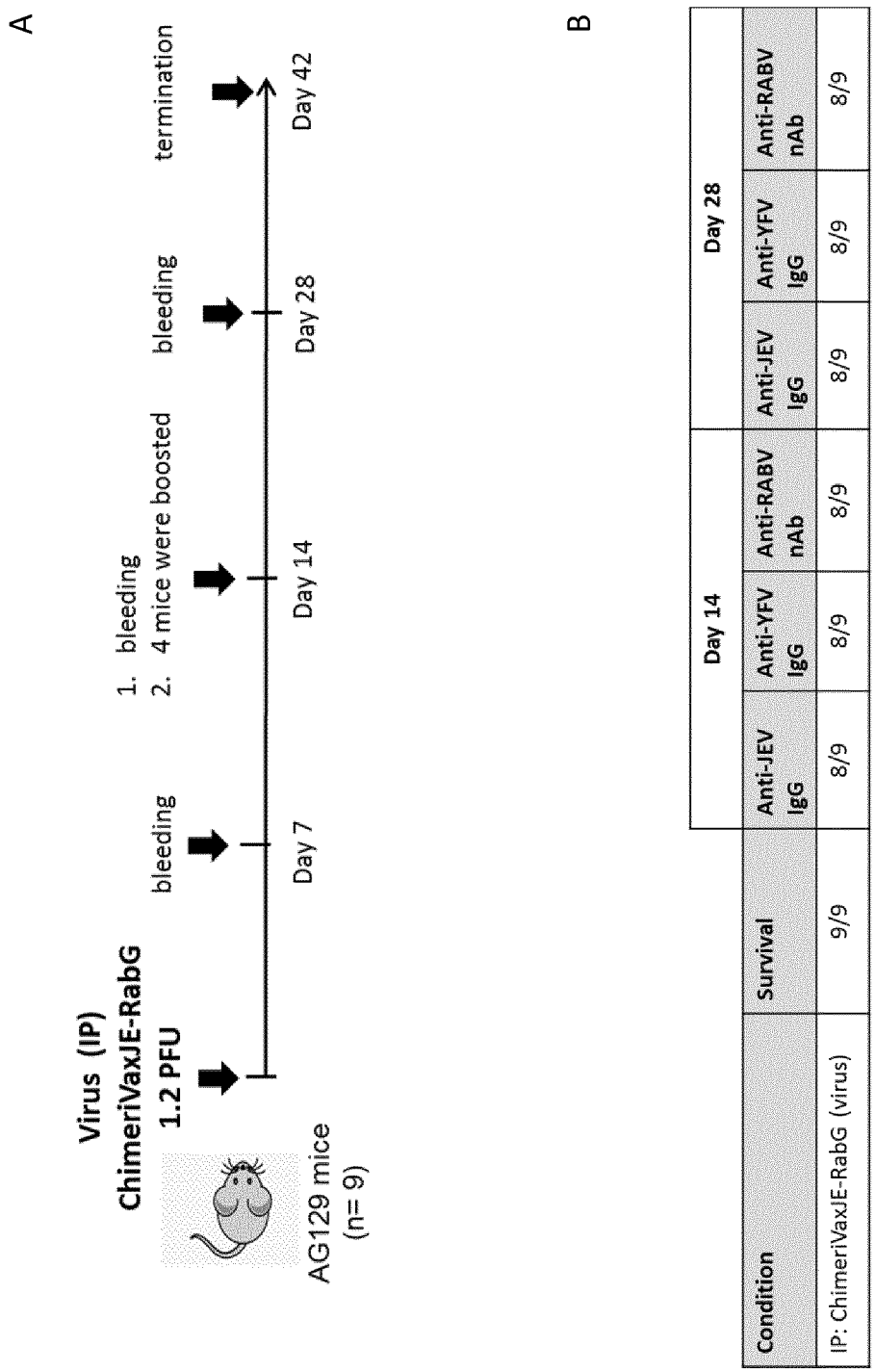

FIG. 13: A) Vaccination schedule to test the immunogenicity of ChimeriVaxJE-RabG in AG129 mice. B) Mortality and serological response to ChimeriVaxJE-RabG in AG129 mice (IP—intraperitoneal).

Figure 14:
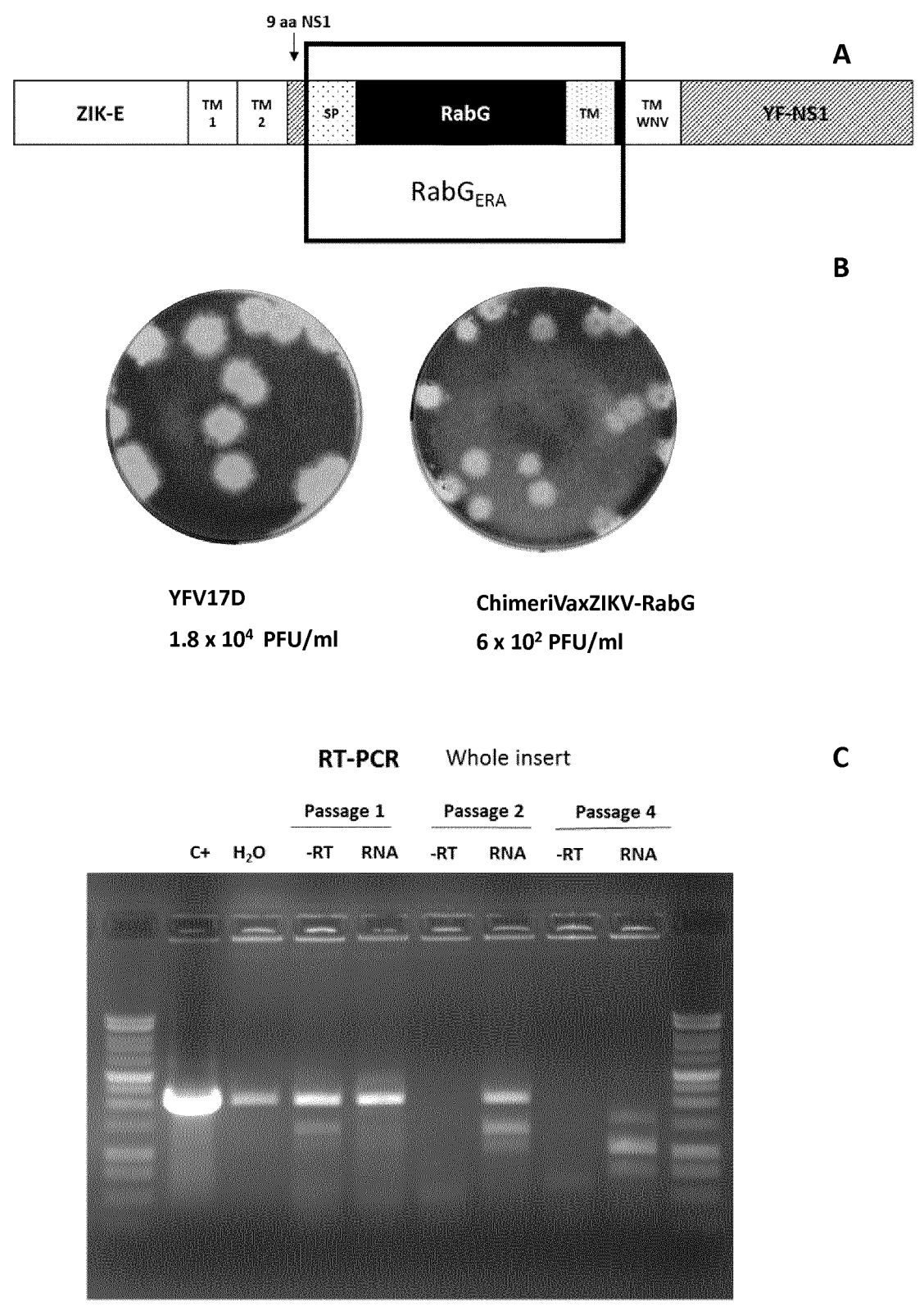

FIG. 14: A) Schematic representation of RabG inserted between ZIK-E and YF-NS1 (ChimeriVaxZIK backbone). B) Plaque phenotype ChimeriVaxZIK-RabG compared to YF17D. C). RT-PCR analysis of the virus samples harvested during serial passaging of the ChimeriVaxZIK-RabG virus. C+, control positive pShuttle-ChimeriVaxZIK-RabG; -RT: RT-PCR reaction without retrotranscriptase; RNA: RT-PCR reaction with the virus RNA.

FIG. 15: A) Vaccination schedule to test the immunogenicity of ChimeriVaxZIK-RabG in AG129 mice. B) Mortality and serological response to ChimeriVaxZIK-RabG in AG129 mice (IP—intraperitoneal).

FIG. 16: Embodiments of backbone modifications.

(A) Flavivirus vector backbones. Schematic representation of the genome organization of typical live-attenuated Flaviviruses used as live vaccines. Each vaccine virus encodes for a backbone (1) comprising the C and NS1-5 genes, and the viral surface proteins prME (2). The components (1) and (2) are known to induce virus specific humoral and cellular immunity; component (2) in particular neutralizing antibodies (nAb).

YF17D—Yellow fever vaccine strain 17D; JE SA14-14-2—Japanese encephalitis vaccine strain SA14-14-2; ZIKV—Zika virus, or live-attenuated Zika virus variant thereof to be used as vaccine.

(B) Prototypic lyssavirus vaccine expressed from a YF17D vector backbone with a variation in Flavivirus surface proteins. Schematic representation of the genome organization of typical live-attenuated Flaviviruses that are transgenic for the rabies virus G protein (RabG, component 3), as protective antigen derived from the prototypic Lyssavirus rabies virus, to be used as vaccine against rabies. Three possible variants are shown using as backbone the components (1) of the YF17D virus, and as Flavivirus surface proteins component (2) from the YF17D, JE SA14-14-2, and ZIKV, respectively.

YF17D-RabG—recombinant YF 17D expressing RabG; CVax-JE-RabG—chimeric YF17D/JE vaccine strain (as disclosed e.g. by Arroyo et al. 2001 PMID: 11134306) expressing RabG; Cvax-ZIK-RabG-YF17D/ZIK vaccine strain (as disclosed e.g. by Kum et al. 2018 PMID: 30564463) expressing RabG.

(C) Antigenic Lyssavirus vaccine variants expressed from a YF17D vector backbone. Schematic representation of the genome organization of typical live-attenuated Flaviviruses that use as backbone the components (1) of the YF17D virus and as transgene component (3) the G protein sequences of a range of Lyssaviruses representing antigenically different phylogroups I (rabies virus), II (Lagos bat virus, LBV; and Mokola virus, MOKV) and III (Lleida bat virus, LLEBV), respectively. Each G protein is considered to be a protective antigen inducing immunity against related Lyssaviruses, at least against viruses belonging to the same phylogroup.

YF17D-RabG—recombinant YF 17D expressing RabG; YF17D-LBV-G—recombinant YF17D-expressing the LBV G-protein; YF17D-MOKV-G—recombinant YF17D-expressing the MOKV G-protein; YF17D-LLEBV—recombinant YF17D-expressing the LLEBV G-protein.

(D) Prototypic Lyssavirus vaccine expressed from a JE SA14-14-2 vector backbone. Schematic representation of the genome organization of live-attenuated Flaviviruses that use as backbone the components (1) of the JE SA14-14-2 virus and as transgene component (3).

The present invention is exemplified for Yellow Fever virus, but is also applicable using other viral backbones of Flavivirus species such, but not limited to, Japanese Encephalitis, Dengue, Murray Valley Encephalitis (MVE), St. Louis Encephalitis (SLE), West Nile (WN), Tick-borne Encephalitis (TBE), Russian Spring-Summer Encephalitis (RSSE), Kunjin virus, Powassan virus, Kyasanur Forest Disease virus, Zika virus, Usutu virus, Wesselsbron and Omsk Hemorrhagic Fever virus.

The invention is further applicable to Flaviviridae, which comprises the genus Flavivirus but also the genera, Pegivirus, Hepacivirus and Pestivirus.

The genus Hepacivirus comprises e.g. Hepacivirus C (hepatitis C virus) and Hepacivirus B (GB virus B)

The genus Pegivirus comprises eg Pegivirus A (GB virus A), Pegivirus C (GB virus C), and Pegivirus B (GB virus D).

The genus Pestivirus comprises e.g. Bovine virus diarrhea virus 1 and Classical swine fever virus (previously hog cholera virus).

The Flavivirus which is used as backbone can itself by a chimeric virus composed of parts of different Flavivirus.

For example the C and NS1-5 region are from Yellow Fever and the prME region is of Japanese encephalitis or of Zika virus. Examples hereof are presented in table 2 and FIG. 16.

The present invention is exemplified for the G protein of Rabies lyssavirus, but is also applicable to G proteins of other Lyssavirus. Examples thereof are Aravan lyssavirus Aravan virus (ARAV), Australian bat lyssavirus, Bokeloh bat lyssavirus, Duvenhage lyssavirus, European bat lyssavirus 1, European bat lyssavirus 2, Ikoma lyssavirus, Irkut lyssavirus, Khujand lyssavirus, Lagos bat lyssavirus, Mokola lyssavirus, Rabies lyssavirus, Shimoni bat lyssavirus and West Caucasian bat lyssavirus, and possible chimeras and antigenic variants thereof. Many of these species occur in bats. The transfer of viruses from bats to humans, is however is significant health risk.

The constructs of the present invention allow a proper presentation of the encoded insert into the ER lumen and proteolytic processing. As exemplified by Rab G protein, the encoded protein by the insert only contains near the C terminus a transmembrane domain which is followed by an peptide which resides in the cytosol. To achieve this configuration, the N terminal signal peptide of Rab G has been removed (or made non-functional). Based on this principle any immunogenic protein can be presented via the vector of the present invention that the protein lacks an N terminal membrane targeted domain and contains at the C terminus a targeting membrane followed by a cytoplasmic sequence to allow the connection with the transmembrane membrane preceding the NS1 protein.

The invention is now further described for embodiments wherein a Flavivirus is used as backbone and a G protein of a lyssavirus as insert.

The G protein of rabies is reviewed in Kuzmina et al. (2013) *J antivir antiretrovir.* 5:2, 37-43. The numbering of features in the sequence is with reference to the mature protein, which is preceded by a signal peptide of 19 AA (MVPQALLFVPLLVFPLCFG) [SEQ ID NO: 18]. Relevant sequence elements in the mature protein are the IIb epitope GCTNLSGFS (AA 34-42) [SEQ ID NO: 15], the transmembrane domain VLLSAGALTALMLIIFLMTCC (AA 440-461) [SEQ ID NO: 19] and the cytoplasmatic domain RRVNRSEPTQHNLRGTGREVSVTPQSGKIISS-WESHKSGGETRL [SEQ ID NO: 20](AA 462-505)

The high sequence identity between G proteins of different Lyssavirus presents no problems to the skilled person to identify in related sequences the sequence elements corresponding to those present in Rabies virus G protein.

Flaviviruses have a positive single-strand RNA genome of approximately 11,000 nucleotides in length. The genome contains a 5' untranslated region (UTR), a long open-reading frame (ORF), and a 3' UTR. The ORF encodes three structural (capsid [C], precursor membrane [prM], and envelope [E]) and seven nonstructural (NS1, NS2A, NS2B, NS3, NS4A, NS4B, and NS5) proteins. Along with genomic RNA, the structural proteins form viral particles. The non-structural proteins participate in viral polyprotein processing, replication, virion assembly, and evasion of host immune response. The signal peptide at the C terminus of the C protein (C-signal peptide; also called C-anchor domain) regulates Flavivirus packaging through coordination of sequential cleavages at the N terminus (by viral NS2B/NS3 protease in the cytoplasm) and C terminus (by host signalase in the endoplasmic reticulum [ER] lumen) of the signal peptide sequence.

The positive-sense single-stranded genome is translated into a single polyprotein that is co- and post translationally cleaved by viral and host proteins into three structural [Capsid (C), premembrane (prM), envelope (E)], and seven non-structural (NS1, NS2A, NS2B, NS3, NS4A, NS4B, NS5) proteins. The structural proteins are responsible for forming the (spherical) structure of the virion, initiating virion adhesion, internalization and viral RNA release into cells, thereby initiating the virus life cycle. The non-structural proteins on the other hand are responsible for viral replication, modulation and evasion of immune responses in infected cells, and the transmission of viruses to mosquitoes. The intra- and inter-molecular interactions between the structural and non-structural proteins play key roles in the virus infection and pathogenesis.

The E protein comprises at its C terminal end two transmembrane sequences, indicated as TM1 and TM2 in e.g. FIG. 6.

NS1 is translocated into the lumen of the ER via a signal sequence corresponding to the final 24 amino acids of E and is released from E at its amino terminus via cleavage by the ER resident host signal peptidase (Nowak et al. (1989) Virology 169, 365-376). The NS1 comprises at its C terminal a 8-9 amino acids signal sequence which contains a recognition site for a protease (Muller & Young (2013) Antiviral Res. 98, 192-208)

The constructs of the present invention are chimeric viruses wherein a Lyssavirus G protein is inserted at the boundary between the E and NS1 protein. However additional sequence elements are provided N terminally and C terminally of the G protein insert.

The invention relates to polynucleotide comprising a sequence of a live, infectious, attenuated Flavivirus wherein a nucleotide sequence encoding at least a part of a Lyssavirus G protein is inserted at the intergenic region between the E and NS1 gene of said Flavivirus, such that a chimeric virus is expressed, characterised in that the encoded sequence C terminally of the E protein of said Flavivirus and N terminal the NS1 protein of said Flavivirus comprises in the following order:

a sequence element allowing the proteolytic processing of the G protein from the E protein by a signal peptidase.
 a lyssavirus G protein comprising a defective functional signal peptide or lacking a functional signal peptide, comprising the IIb epitope, comprising the C terminal TM membrane and comprising the C terminal cytoplasmatic sequence, and
 a TM2 domain of a flaviviral E protein.

To allow proteolytic processing of the lyssavirus G protein from the Flavivirus E protein at its aminoterminal end and allow proteolytic processing of the lyssavirus G protein from the Flavivirus NS1 protein at its C terminal, sequence elements are provided which are substrates for a signal peptidase. These can vary in length and in sequence, and can be as short as one amino acid as shown in Jang et al. cited above. A discussion on suitable recognition sites for signalling proteases is found in Nielsen et al. (1997) Protein Eng. 10, 1-6.

Typically, at the C terminus of the G protein, the signal peptide at the N terminus of the NS1 protein will be used (or a fragment which allows proteolytic processing).

Typically, at the N terminus of the G protein, the same signal peptide (or fragment) of the NS1 protein of the Flavivirus backbone is introduced.

The invention equally relates to polynucleotides comprising a sequence of a live, infectious, attenuated Flavivirus. Herein a nucleotide sequence encoding at least a part of a Lyssavirus G protein is inserted at the intergenic region between the E and NS1 gene of said Flavivirus. Additional sequences are provided such that when the chimeric virus is expressed such that the encoded sequence from the C terminally of the E protein to the N terminus of the signal peptide of the NS1 protein comprises in the following order:
- a further signal peptide (or cleavable fragment thereof) of a Flavivirus NS1 gene, C terminal to the E protein and N terminal to the NS1 protein.
- a lyssavirus G protein comprising a defective functional signal peptide or lacking a functional signal peptide, comprising the IIb epitope, comprising the C terminal TM membrane and the C terminal cytoplasmatic sequence. This G protein is C terminally positioned from a NS1 signal peptide. C terminally of the G protein is the sequence of a Flavivirus TM2 transmembrane domain of a Flavivirus. C terminally of this TM2 sequence follows the NS1 protein, including its native signal peptide sequence.

Thus, the G protein and the TM2 domain are flanked at N terminus and C terminus by an NS1 sequence. In the embodiments disclosed in the examples the protein and DNA sequence of both NS1 are identical.

In typical embodiments both NS1 signal sequences have the sequence DQGCAINFG [SEQ ID NO:6].

The constructs of the present invention did not show recombination due to the presence of this repetitive sequence. Sequence modifications can be introduced or NS1 sequences from different Flavivirus can be used to avoid presence of identical sequences, as long as the encoded peptide remains a target from the protease which processes these NS1 Nterminal signal sequences.

In typical embodiments, as disclosed in the examples, the G protein is of Rabies virus, preferably of the ERA strain of Rabies virus.

To facilitate the production of virus in the mammalian hosts, the nucleotide sequence of the G protein is codon optimized.

The G protein in the constructs of the present invention provides immunogenicity when the IIb epitope is present. The IIb epitope of Rabies virus typically has the sequence

GCTNLSGFS. [SEQ ID NO: 15]

Furthermore to obtain the desired topology of the Rabies G protein during processing of the virus, the presence of the transmembrane sequence of the G protein is required, as well as the C terminal cytoplasmatic sequence. The sequences of TM domain and cytoplasmatic sequence of the G protein are typically those of respectively amino acids 440-461 and amino acids 462-505 of rabies G protein.

It is submitted that minor sequence modifications in the G protein and in the C terminal tail can be introduced without loss of function of these sequence elements. For example, amino acids substitutions wherein hydrophobic side chains are preserved in the transmembrane domain, or truncated versions of the cytoplasmic domain with sufficient length to allow proper localisation of the transmembrane domains at the N terminus and C terminus of the cytoplasmatic domain.

It has been found that the presence of a functional signal peptide of the G protein results in a selective pressure whereby a part of the G protein comprising its signal peptide is deleted or mutated. Thus the constructs of the present invention typically contain a defective G protein signal by partial or complete removal of this sequence or by the introduction of mutations which render the signal protein non-functional (such as the Rab G F145 mutation in the signal peptide MVPQALLFVPLLVFPLCFG [SEQ ID NO 18])

The TM domain which is located C terminally of the G protein and N terminally of the NS1 is generally of a Flavivirus, typically from the E protein, and more typical a TM2 domain of an E protein. In preferred embodiments this TM2 domain of an E protein is from a different Flavivirus than the virus forming the backbone. The examples of present invention describe the TM2 domain of the E protein of the West Nile virus. This domain has the sequence RSIAMTFLAVGGVLLFLSVNVHA [SEQ ID NO 13].

In the examples section below and in the schematic representation all sequence elements form a continuous sequence without any intervening sequence elements. It is submitted that in between these sequence elements, additional amino acids may be present as long as the localisation of the protein at either the ER lumen or cytosol is not disturbed and proteolytic processing is maintained.

The above described nucleotide sequence can be that of the virus itself or can refer to a sequence in a vector. A suitable vector for cloning Flavivirus and chimeric version are Bacterial Artificial Chromosomes, as describe in more detail below.

The methods and compounds of the present invention have medicinal application, whereby the virus or a vector encoding the virus can be used to vaccinate against the lyssavirus which contains the G protein that was cloned in the Flavivirus. In addition, the proteins from the Flavivirus equally provide protection such that the compounds of the present invention can be used to vaccinate against a Flavivirus and a lyssavirus using a single virus or DNA vaccine.

The use of Bacterial Artificial Chromosomes, and especially the use of inducible BACS as disclosed by the present inventors in WO2014174078, is particularly suitable for high yield, high quality amplification of cDNA of RNA viruses such as chimeric constructs of the present invention.

A BAC as described in this publication BAC comprises:
- an inducible bacterial ori sequence for amplification of said BAC to more than 10 copies per bacterial cell, and
- a viral expression cassette comprising a cDNA of an the RNA virus genome and comprising cis-regulatory elements for transcription of said viral cDNA in mammalian cells and for processing of the transcribed RNA into infectious RNA virus.

As is the case in the present invention the RNA virus genome is a chimeric viral cDNA construct of an RNA virus genome and a rabies G protein.

In these BACS, the viral expression cassette comprises a cDNA of a positive-strand RNA virus genome, an typically
- a RNA polymerase driven promoter preceding the 5' end of said cDNA for initiating the transcription of said cDNA, and
- an element for RNA self-cleaving following the 3' end of said cDNA for cleaving the RNA transcript of said viral cDNA at a set position.

The BAC may further comprise a yeast autonomously replicating sequence for shuttling to and maintaining said bacterial artificial chromosome in yeast. An example of a yeast ori sequence is the 2μ plasmid origin or the ARS1 (autonomously replicating sequence 1) or functionally homologous derivatives thereof.

The RNA polymerase driven promoter of this first aspect of the invention can be an RNA polymerase II promoter, such as Cytomegalovirus Immediate Early (CMV-IE) promoter, or the Simian virus 40 promoter or functionally homologous derivatives thereof.

The RNA polymerase driven promoter can equally be an RNA polymerase I or III promoter.

The BAC may also comprise an element for RNA self-cleaving such as the cDNA of the genomic ribozyme of hepatitis delta virus or functionally homologous RNA elements.

The formulation of DNA into a vaccine preparation is known in the art and is described in detail in for example chapter 6 to 10 of "DNA Vaccines" Methods in Molecular Medicine Vol 127, (2006) Springer Saltzman, Shen and Brandsma (Eds.) Humana Press. Totoma, N.J. and in chapter 61 Alternative vaccine delivery methods, P 1200-1231, of Vaccines (6th Edition) (2013) (Plotkin et al. Eds.). Details on acceptable carrier, diluents, excipient and adjuvant suitable in the preparation of DNA vaccines can also be found in WO2005042014, as indicated below.

"Acceptable carrier, diluent or excipient" refers to an additional substance that is acceptable for use in human and/or veterinary medicine, with particular regard to immunotherapy.

By way of example, an acceptable carrier, diluent or excipient may be a solid or liquid filler, diluent or encapsulating substance that may be safely used in systemic or topic administration. Depending upon the particular route of administration, a variety of carriers, well known in the art may be used. These carriers may be selected from a group including sugars, starches, cellulose and its derivatives, malt, gelatine, talc, calcium sulphate and carbonates, vegetable oils, synthetic oils, polyols, alginic acid, phosphate buffered solutions, emulsifiers, isotonic saline and salts such as mineral acid salts including hydrochlorides, bromides and sulphates, organic acids such as acetates, propionates and malonates and pyrogen-free water.

A useful reference describing pharmaceutically acceptable carriers, diluents and excipients is Remington's Pharmaceutical Sciences (Mack Publishing Co. N. J. USA, (1991)) which is incorporated herein by reference.

Any safe route of administration may be employed for providing a patient with the DNA vaccine. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intramuscular and subcutaneous injection may be appropriate, for example, for administration of immunotherapeutic compositions, proteinaceous vaccines and nucleic acid vaccines. It is also contemplated that microparticle bombardment or electroporation may be particularly useful for delivery of nucleic acid vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

DNA vaccines suitable for oral or parenteral administration may be presented as discrete units such as capsules, sachets or tablets each containing a pre-determined amount of plasmid DNA, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the DNA plasmids with liquid carriers or finely divided solid carriers or both, and then, if necessary, shaping the product into the desired presentation.

The above compositions may be administered in a manner compatible with the dosage formulation, and in such amount as is effective. The dose administered to a patient, should be sufficient to effect a beneficial response in a patient over an appropriate period of time. The quantity of agent (s) to be administered may depend on the subject to be treated inclusive of the age, sex, weight and general health condition thereof, factors that will depend on the judgement of the practitioner.

Furthermore DNA vaccine may be delivered by bacterial transduction as using live-attenuated strain of Salmonella transformed with said DNA plasmids as exemplified by Darji et al. (2000) *FEMS Immunol Med Microbiol* 27, 341-349 and Cicin-Sain et al. (2003) *J Virol* 77, 8249-8255 given as reference.

Typically the DNA vaccines are used for prophylactic or therapeutic immunisation of humans, but can for certain viruses also be applied on vertebrate animals (typically mammals, birds and fish) including domestic animals such as livestock and companion animals. The vaccination is envisaged of animals which are a live reservoir of viruses (zoonosis) such as monkeys, dogs, mice, rats, birds and bats.

In certain embodiments vaccines may include an adjuvant, i.e. one or more substances that enhances the immunogenicity and/or efficacy of a vaccine composition However, life vaccines may eventually be harmed by adjuvants that may stimulate innate immune response independent of viral replication. Non-limiting examples of suitable adjuvants include squalane and squalene (or other oils of animal origin); block copolymers; detergents such as Tween-80; Quill A, mineral oils such as Drakeol or Marcol, vegetable oils such as peanut oil; Corynebacterium-derived adjuvants such as Corynebacterium parvum; Propionibacterium-derived adjuvants such as Propionibacterium acne; Mycobacterium bovis (Bacille Calmette and Guerin or BCG); interleukins such as interleukin 2 and interleukin 12; monokines such as interleukin 1; tumour necrosis factor; interferons such as gamma interferon; combinations such as saponin-aluminium hydroxide or Quil-A aluminium hydroxide; liposomes; ISCOMt) and ISCOMATRIX (B) adjuvant; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol'EMA; acrylic copolymer emulsions such as Neocryl A640; vaccinia or animal poxvirus proteins; sub-viral particle adjuvants such as cholera toxin, or mixtures thereof.

EXAMPLES

Example 1

Insertion of Rab G in E/NS1

1.1. PLLAV-YFV17D-RabG-ERA

A first construct carrying full length RabG (ERA strain) inserted in the intergenic region between YF-E/NS1 genes was cloned as follows: first 9 amino acids of NS1 (27 nucleotides) were added before the RabG signal peptide (SP) to reproduce the signal peptidase cleavage site between E and NS1 and allow the release of RabG protein, the RabG C terminus was preserved and fused to WNV-E second transmembrane domain (FIG. 1A).

The sequence analysis of the serial passage and the plaque-purified YFV17D-RabG-ERA(E/NS1) virus revealed a 246 bp deletion (82 aa) at the beginning of the ERA-RabG coding sequence which indicates that the construct is not stable. This deletion starts in the first amino acid of the signal peptide (SP) of RabG and involves the loss of part of epitope II as well as some of the disulfide bridges that are required for protein folding. However, this live-attenuated YFV-ERA-RabG(E/NS1) virus was able to induce neutralizing antibodies against RABV in mice, which seroconverted to both YF and rabies (FIG. 1C). Since this Δ82-ERA-RabG protein seemed to be immunogenic, the cDNA derived from plaque-purified virus was cloned into the above described BAC vector with inducible ori (PLLAV-YFV17D). Four variants carrying different mutations were detected after sequencing of 13 E.coli clones (pSYF17D-Δ82-ERA-RabG-ENS1 #1, #2, #9 and #12, respectively, FIG. 2). Each of these new pSYF17D-Δ82-ERA-RabG(E/NS1) constructs were transfected in BHK21J cells. All of them showed a consistent induction of a typical virus-induced cytopathogenic effect (CPE). Likewise, the virus supernatants, harvested from transfected cells, contained infectious particles able to form characteristic viral lysis plaques (FIG. 2). Plaque-purified virus that also had been used to generate cDNA was inoculated into AG129 mice and although there was seroconversion for YF, no neutralization antibodies against rabies virus were detected (FIG. 3). Therefore, further in vitro and/or in vivo characterization of these constructs was not pursued.

1.2. PLLAV-YFV17D-RabG-CVS

It has been shown that ERA-RabG protein induced a marked apoptosis (Préhaud et al. (2003) *J Virol.* 77, 10537-10547). A codon optimized full length RabG from the non-apoptotic rabies challenge virus strain is (CVS) inserted between E/NS1, in the same configuration as described for the ERA strain (FIG. 4A).

This construct was transfected in BHK-21J and virus-induced CPE was observed. Tissue derived virus supernatant was able to induce CPE and plaques (FIG. 4B). Further characterization of three plaque purified viruses derived from this construct revealed that in this case there was no deletions in the RabG sequence but a single point nucleotide mutation in the signal peptide of RabG protein was detected. This mutation changed the amino acid phenylalanine to serine (F14S). Tissue cultured virus supernatant harvested after transfection with the construct and plaque purified virus were inoculated into AG129 mice to determine immunogenicity. All the mice were seroconverted to both RABV and YFV (FIG. 5). Therefore, as this CVS-RabG-F14S showed to be immunogenic, cDNA derived from plaque-purified virus was cloned into pShuttle-YF17D (PLLAV) and this new construct was characterized as explained above for the previous constructs (CPE and plaque phenotyping) showing that was able to launch viable and fully replication-competent recombinant transgenic vaccine viruses. PLLAV-YFV17D-RabG-CVS-F14S in parallel with plaque purified virus YF17D-CVS-RabG-F14S were injected into AG129 mice (n=10) and 4/10 animals and 9/10 were seroconverted to both RABV and YFV respectively (table 1 and FIG. 11). This result suggested that still further optimization of the PLLAV was required to improve the immunogenicity of the PLLAV YF17D-RabG (E/NS1).

The examples above indicated that there is a pressure to obtain non-functional variants of the original Rab G protein signal peptide by ether deletion of the entire signal peptide, or by introducing mutations in the signal peptide.

Therefore, new sYF17D-RabG constructs were generated wherein the RabG SP sequence was deleted to improve the immunogenicity of the expressed RabG protein.

Example 2

PLLAV YF17D-RabG-ΔSP (E/NS1) Constructs

The signal peptide of Rab G is involved in the immunogenicity of the protein. The RabG protein needs to be accommodate in the overall topology of the YF polyprotein to allow a proper expression of the transgene and replication of the YFV vector (FIG. 6). The presence of full length RabG SP adds one extra transmembrane into the viral construct that disturbs the YF polyprotein conformation and affects the native folding of RabG that is required for full antigenicity.

An optimized construct carrying $RabG_{ERA}\Delta SP$ (FIG. 3) was generated and characterized in vitro as described previously (FIG. 7A). Co-expression of RabG along with the YFV polyprotein could be confirmed (FIG. 7B) indicating proper folding of RabG. Compared to the construct as depicted in FIG. 1A and described in example 1 the sequence encoding the 19 Nterminal amino acids has been deleted The stability of pShuttle-YF17D-$RabG_{ERA}\Delta SP$ derived viruses was determined by performing RT-PCR to detect the transgene insert in virus samples that were harvested during serial passaging of the YF17D-$RabG_{ERA}\Delta SP$ virus (FIG. 8). Sequencing of the RT-PCR products showed that N-terminally truncated RabG insert can be detected until passage 7 with no mutations.

The immunogenicity of the BAC construct PLLAV-YF17D-$RabG_{ERA}\Delta SP$ was assessed in vivo in AG129 mice (n=5) post IP inoculation with the recombinant virus obtained after transfecting cells with this PLLAV (FIG. 9A). All the animals vaccinated with the virus derived from this N terminal truncated RabG construct were seroconverted for both YFV and RABV, after single vaccination. Serum neutralizing antibody (SNA) titres against rabies were also found to be greater than 10 IU/ml The titre subsequently increased after each booster (FIG. 9B).

To confirm the results obtained with YF17D-$RabG_{ERA}\Delta SP$ virus and to evaluate the immunogenicity of its corresponding inducible BAC in vivo, we performed a new experiment in parallel with the commercially available rabies virus vaccine Rabipur® post single (day 0) and double (day −7 and day 0) vaccination (FIG. 10). Considering the immunogenic nature of first generation construct YF17D-CVS-RabG-F14S, we also included PLLAV- YF17D-CVS-RabG-F14S BAC in the study (see B.1 section). YFV-17-NLuc was used as positive control for YF vaccination (Table-3). All the manipulations were performed IP.

For the first time, the serological analysis revealed that not only the YFV17D-RabG viruses but also the corresponding BAGS were able to induce anti-YFV and anti-RABV antibodies (Table 1 and FIG. 11). The BAC construct PLLAV-YF17D-RabG$_{ERA}$ΔSP was equally potent to YF17D-RabG$_{ERA}$ΔSP virus vaccine for inducing both anti-YFV and anti-RABV specific antibodies in efficiency (n=9/10 vs. n=8/9 for BAC vs. virus vaccine on day 21 post vaccination) as well as kinetics (induction of antibodies only 7 days post vaccination). As it was expected, all the animals vaccinated with YFV-17D-NLuc or Rabipur were seroconverted for YFV or RABV at day 7- or day 14-post vaccination, respectively. YFV17D-RabG-CVS-F14S virus vaccine also induced an equally potent immune response like YFV17D-RabG$_{ERA}$ΔSP in efficiency (dual immune response toward YFV and RABV in n=9/10 animals 21 days post vaccination) but with a delayed kinetics (dual immune response 14 days post vaccination). Furthermore, PLLAV-YFV17D-RabG-CVS-F14S also induced dual immune responses against YFV and RABV, however this was markedly less efficient (n=4/10) and slower in kinetics (starts 21 days post vaccination) compared to the optimized construct. Single vaccination with Rabipur, YF17D-RabG$_{ERA}$ΔSP and BAC construct PLLAV-YF17D-RabG$_{ERA}$ΔSP were able to induce similar dual immune response in efficiency (>90% animals 7 days post vaccination) as well as magnitude (14 days post vaccination). Although, single vaccination with Rabipur was quicker than YF17D-RabG$_{ERA}$ΔSP and BAC construct PLLAV-YF17D-RabG$_{ERA}$ΔSP (SNA; 10 IU/ml 7 days vs. 14 days post vaccination, respectively), however, all the animals revealed significantly higher immune response than the WHO recommended protective titer (0.5 IU/ml) post vaccination. Double vaccination regimen of Rabipur (day −7 and day 0) revealed significantly higher immune response against RABV compared to single YF17D-RabG$_{ERA}$ΔSP and BAC constrcuct PLLAV-YF17D-RabG$_{ERA}$ΔSP vaccinations. This indicates that the comparative lower immune response to Rabipur is rather related to optimizing the efficient dose of YF17D-RabG$_{ERA}$ΔSP and PLLAV-YF17D-RabG$_{ERA}$ΔSP for vaccination and could be optimized in dose escalation studies.

TABLE 1

Mortality and serological response to second generation YFV-RabG constructs in AG129 mice

| | survival | Day 7 | | Day 14 | | Day 21 | | Day 28 | |
|---|---|---|---|---|---|---|---|---|---|
| | | Anti-YFV-IgG | Anti-RABV nb | Anti-YFV-IgG | Anti-RABV nb | Anti-YFV-IgG | Anti-RABV nb | Anti-YFV-IgG | Anti-RABV nb |
| IP: * rabipur™ 2-shots | 6/6 | 0/6 | 6/6 | 0/6 | 6/6 | 0/6 | 6/6 | 0/6 | 6/6 |
| IP: * rabipur™ 1-shot | 6/6 | 0/6 | 6/6 | 0/6 | 6/6 | 0/6 | 6/6 | 0/6 | 6/6 |
| IP: YFV17D-NLuc | 5/6 | 5/6 | 0/6 | 6/6 | 0/6 | 6/6 | 0/6 | 5/5 | 0/5 |
| IP: YFV17D-RabG-ERA | 9/10 | 9/10 | 9/10 | 8/9 | 8/9 | 8/9 | 8/9 | 8/9 | 8/9 |
| IP: PLLAV YFV17D-RabG-ERA-(ΔSP) | 10/10 | 8/10 | 7/10 | 8/10 | 8/10 | 9/10 | 9/10 | 9/10 | 9/10 |
| IP: YFV17D-RabG-CVS-F14S | 9/10 | 0/10 | 0/10 | 7/10 | 5/10 | 10/10 | 9/10 | 10/10 | 9/10 |
| IP: PLLAV-YF-RabG-CVS-F14S | 10/10 | 0/10 | 0/10 | 0/10 | 0/10 | 6/10 | 4/10 | 6/10 | 4/10 |

* Rabipur™ 2-shots: these mice were vaccinated with Rabipur™ and 7 days later were boosted in the same conditions. Hence, Day 7, 14, 21 and 28 for these animals correspond with 7, 14, 21 and 28 days after booster.

In addition to PLLAV-YFV17D-RabG$_{ERA}$ΔSP, a similar construct (ΔSP) carrying the RabG sequence from CVS strain was generated. Furthermore, it has been described in the literature (Bonaldo et al. (2007) cited above; Trindade et al. (2012) *Mem Inst Oswaldo Cruz* 107, 262-272) that it might be possible that the protein inserted between E and NS1 YF-proteins could be retained in the ER due to retention signals found in the YFV, or generally Flavivirus, transmembrane domains (Op De Beeck et al (2004) *J Virol.* 78, 12591-125602; Op De Beeck et al. (2003) *J Virol.* 77, 813-820) at the end of the insert described in those papers. Although we have preserved the original transmembrane domain of RabG in our constructs which has different signals than YF TM1, we cloned two PLLAVs more (ERA-ΔSP and CVS-ΔSP RabG) in which a 2A self-cleaving peptide was added at the end of the cytoplasmatic tail of RabG to compensate for the ER retention signal.

Unexpectedly and in contrast to the optimal RabG expression suggested by Giel-Moloney et al. 2017 (cited above), the replication competence of the YFV17D-RabG$_{ERA}$ΔSP/2A was much lower compared if to the YFV17D-RabG$_{ERA}$ΔSP virus lacking 2A regarding virus yields following BAC transfection into BHK21J cells, as measured by virus titration exemplified by titers of 0.8-1.4×10$^4$ TCID$_{50}$/mL for YFV17D-RabG$_{ERA}$ΔSP/2A and 8×10$^5$ TCID$_{50}$/mL for YFV17D-RabG$_{ERA}$ΔSP, respectively. A similar reduction of virus yields was seen for pShuttle-YFV17D-RabG$_{CVS}$ΔSP/2A versus pShuttle-YFV17D-RabG$_{CVS}$ΔSP.

However, AG129 mice (n=9) vaccinated with YFV17D-RabG$_{ERA}$ΔSP/2A (virus) seroconverted for both rabies and YF (7 out of 9 mice).

Example 3

ChimeriVax-JE-RabG

Based on the knowledge obtained with the generation PLLAV-YF17D-RabG$_{ERA}$ΔSP (FIG. 6, an optimized rabies/ChimeriVax-JE PLLAV vaccine construct was generated carrying the optimized G protein sequence (RabG$_{ERA}$ΔSP). It is expected that this construct induces specific immune responses against RABV, JEV and YFV.

The RabG$_{ERA}$ΔSP sequence was introduced in the PLLAV ChimeriVax-JE backbone to generate a PLLAV ChimeriVaxJE-RabG vaccine construct (FIG. 12A). This PLLAV ChimeriVax-JE carries the prME (surface glycoprotein) coding region of the Japanese encephalitis LAV virus (JE SA14-14-2). The RabG$_{ERA}$ΔSP sequence was inserted between the JE-E and YF17D-NS1 genes.

PLLAV ChimeriVaxJE-RabG was transfected into BHK21J cells and typical CPE was observed as well as the virus supernatant harvested from them formed markedly smaller plaques compared to the plaque phenotype of YFV17D (FIG. 12B). Therefore, the resulting chimeric (JEV/YFV) transgenic (RabG) virus is further attenuated, and virus yields from the rabies/chimeric (JEV/YFV) PLLAV construct were at least 100-fold less than from the homologous rabies/YFV PLLAV.

The stability of PLLAV ChimeriVaxJE-RabG was determined by performing RT-PCR to detect the transgene insert in virus samples that were harvested during serial passaging of the ChimeriVaxJE-RabG virus (FIG. 12C). Sequencing of the RT-PCR products showed that RabG insert with no mutations can be detected at least until passage 4 (further passages will be analyzed).

Regarding the immunogenicity of PLLAV-ChimeriVaxJE-RabG, the recombinant virus obtained after transfecting cells with this PLLAV was assessed in vivo in AG129 mice (n=9) post IP inoculation (FIG. 13A). The JEV-, YFV- and RABV-specific antibody responses were quantified by indirect immunofluorescence assay (IIFA) (Euroimmune YFV and JEV) and/or serum neutralization assay (SNA) (JEV and RABV).

Vaccinated mice were monitored daily for morbidity/mortality and blood was sampled for serological analysis at baseline and with two-week intervals. Some animals (4 of the 9 mice) were boosted two weeks after first inoculation with the ChimeriVaxJE-RabG (virus) using same dose and route than in the first vaccination (FIG. 13A).

The immunogenicity analysis for ChimeriVaxJE-RabG revealed that eight out of nine mice vaccinated by IP administration of cell culture-derived virus seroconverted for JEV, YFV and RABV at 14 days post vaccination (FIG. 13B). Moreover, anti-RABV antibodies above 0.5 IU/ml could be detected in two of the virus-vaccinated mice at day 7 post-vaccination and in 4 animals antibody titer of 0.48 IU/ml was observed already at the same time. Of note, according to WHO guidelines a minimum serum antibody concentration of 0.5 IU/ml is used as a measure of adequate seroconversion after vaccination. Furthermore, JEV SNA test (serum samples harvested at day 42 post vaccination) confirmed the presence of neutralizing antibodies against JEV in those 8 mice in which binding antibodies were detected by IIFA. Furthermore, regarding vaccine safety, no mortality was observed after inoculation of AG129 mice with the vaccine virus.

These results showed that even a dose as low as 1.2 PFU induced a potent immune response against the three virus: JEV, RABV and YFV.

Example 4

ChimeriVax-ZIK-RabG

Similar as described for PLLAV ChimeriVaxJE-RabG an optimized rabies/ChimeriVax-ZIKV PLLAV vaccine construct was generated carrying the optimized G protein sequence (RabG$_{ERA}$ΔSP).). It is expected that this construct induces specific immune responses against RABV, ZIKV and YFV.

This RabG$_{ERA}$ΔSP sequence was introduced in the PLLAV ChimeriVax-ZIKV backbone to generate a PLLAV ChimeriVaxZIKV-RabG vaccine construct (FIG. 14A). This PLLAV ChimeriVax-ZIKV carries the prME (surface glycoprotein) coding region of the Zika virus (Asian lineage, Yap Island 2007, Genbank EU545988). The RabG$_{ERA}$ΔSP sequence was inserted between the ZIKV-E and YF17D-NS1 genes.

PLLAV ChimeriVaxZIKV-RabG was transfected into BHK21J cells and typical CPE was observed as well as the virus supernatant harvested from them formed markedly smaller plaques compared to the plaque phenotype of YFV17D (FIG. 14B). Therefore, the resulting chimeric (ZIKV/YFV) transgenic (RabG) virus is further attenuated, and virus yields from the rabies/ZIKV PLLAV construct were at least 100-fold less than from the homologous rabies/YFV PLLAV.

The stability of PLLAV ChimeriVaxZIKV-RabG was determined by performing RT-PCR to detect the transgene insert in virus samples that were harvested during serial passaging of the ChimeriVaxJE-RabG virus (FIG. 14C). Sequencing of the RT-PCR products showed that RabG insert with no mutations could be detected until passage 2.

The immunogenicity of the construct PLLAV-ChimeriVaxZIKV-RabG and the recombinant virus obtained after transfecting cells with this PLLAV was assessed in vivo in AG129 mice (n=5) post IP inoculation (FIG. 15A). The ZIKV-, YFV- and RABV-specific antibody responses were quantified by indirect immunofluorescence assays (IIFA) (Euroimmune YFV and ZIKV) and/or serum neutralization assays (SNA) (ZIKV and RABV).

Vaccinated mice were monitored daily for morbidity/mortality and blood was sampled for serological analysis at baseline and with two-week intervals.

The immunogenicity analysis for ChimeriVaxZIKV-RabG revealed that all mice vaccinated with cell culture-derived virus (i.p.) seroconverted for ZIKV, YFV and RABV at 17 days post vaccination (FIG. 15B). ZIKV SNA performed at day 28 post-vaccination (data not shown) confirmed the presence of neutralizing antibodies against ZIKV in 4 of 5 mice vaccinated with the cell culture-derived virus that were positive for binding antibodies (IIFA).

Furthermore, regarding vaccine safety, no mortality was observed after inoculation of AG129 mice with the vaccine virus.

In conclusion, ChimeriVaxZIKV-RabG induced a potent immune response against ZIKV, YFV and RABV virus in spite of being fairly attenuated in comparison with YF17D-RabG.

Example 5

Construct with Chimeric Flavivirus Backbone

Different constructs are made which comprise Lyssavirus G proteins, and wherein the backbone of the Flavivirus is itself a chimer of two different Flavivirus. FIG. 16 shows an overview of exemplary constructs wherein the backbone can comprise parts of Yellow Fever virus, Zika virus or Japanese encephalitis virus.

This allows to produce vaccines which provide protection against a lyssavirus and more than one Flavivirus. This is illustrated in Table 2, wherein is indicated which parts of the vaccine provide humoral immunity, cell mediated immunity and neutralising antibodies.

TABLE 2

Immune responses of constructs with chimeric backbone

| Construct No. | Humoral immunity against Lyssavirus G protein (3) | CMI against Lyssavirus G protein (3) | nAb against Flavivirus prME (2) | Humoral immunity against backbone (1) | CMI against backbone (1) |
|---|---|---|---|---|---|
| A1 | None | None | YFV | YFV | YFV |
| A2 | None | None | JEV | JEV | JEV |
| A3 | None | None | ZIKV | YFV | YFV |
| B1 | RabG | RabG | YFV | YFV | YFV |
| B2 | RabG | RabG | JEV | YFV | YFV |
| B3 | RabG | RabG | ZIKV | YFV | YFV |
| C1 (=B1) | phylogroup I | phylogroup I | YFV | YFV | YFV |
| C2 | phylogroup II | phylogroup II | YFV | YFV | YFV |
| C3 | phylogroup II | phylogroup II | YFV | YFV | YFV |
| C4 | phylogroup III | phylogroup III | YFV | YFV | YFV |
| D1 | RabG | RabG | JEV | JEV | JEV |

[RabG—rabies virus G protein; CMI—cell mediated immunity; nAb—neutralizing antibody; prME—Flavivirus surface glycoproteins; YFV—yellow fever virus]

```
OVERVIEW OF SEQUENCES DEPICTED IN THE APPLICATION
                                                    SEQ ID NO: 1
                                                    SEQ ID NO: 2
GGA AAG TTG TTC ACT CAG ACC ATG AAA GGC GTG GAA CGC CTG GCC
 G   K   L   F   T   Q   T   M   K   G   V   E   R   L   A

GTC ATG GGA GAC ACC GCC TGG GAT TTC AGC TCC GCT GGA GGG TTC
 V   M   G   D   T   A   W   D   F   S   S   A   G   G   F

TTC ACT TCG GTT GGG AAA GGA ATT CAT ACG GTG TTT GGC TCT GCC
 F   T   S   V   G   K   G   I   H   T   V   F   G   S   A

TTT CAG GGG CTA TTT GGC GGC TTG AAC TGG ATA ACA AAG GTC ATC
 F   Q   G   L   F   G   G   L   N   W   I   T   K   V   I
                         ─────────────────────────────────
                                    YFE TM1

ATG GGG GCG GTA CTT ATA TGG GTT GGC ATC AAC ACA AGA AAC ATG
 M   G   A   V   L   I   W   V   G   I   N   T   R   N   M
─────────────────────────────────────────────────────────

ACA ATG TCC ATG AGC ATG ATC TTG GTA GGA GTG ATC ATG ATG TTT
 T   M   S   M   S   M   I   L   V   G   V   I   M   M   F
─────────────────────────────────────────────────────────
YFE TM2

TTG TCT CTA GGA GTT GGc GCc GAC CAG GGC TGC GCG ATA AAT TTC
 L   S   L   G   V   G   A   D   Q   G   C   A   I   N   F
─────────────────────        ───────────────────────────────
                                    9 aa NS1

GGT aaa ttt cca ata tac aca att ccc gac aaa ctt gga ccc tgg
 G   K   F   P   I   Y   T   I   P   D   K   L   G   P   W agt ccg ata gac att cac cat ttg tct tgc cct aat aac ctt gtg
 S   P   I   D   I   H   H   L   S   C   P   N   N   L   V gtt gag gac gag ggg tgt act aac ttg agt ggg ttc
 V   E   D   E   G   C   T   N   L   S   G   F C terminal part of YF-E protein
                                                    SEQ ID NO: 3
GKLFTQTMKGVERLAVMGDTAWDFSSAGGFFTSVGKGIHTVFGSAFQGLFGGLNWITKV

IMGAVLIWVGINTRNMTMSMSMILVGVIMMFLSL

YFE-TM1
                                                    SEQ ID NO: 4
GGLNWITKVIMGAVLIWVGINT
```

OVERVIEW OF SEQUENCES DEPICTED IN THE APPLICATION

YFE-TM2
SEQ ID NO: 5
MTMSMSMILVGVIMMFLSLGVGA

NS1 N terminal 9 AA
SEQ ID NO: 6
DQGCAINFG

Nterminal part of Rab G (without signal peptide)
SEQ ID NO: 7
KFPIYTIPDKLGPWSPIDIHHLSCPNNLVVEDEGCTNLSGF

SEQ ID NO: 8
SEQ ID NO: 9

```
aat caa gtt tct gga gtc gac ctc gga ttg cca aat tgg ggg aag
 N   Q   V   S   G   V   D   L   G   L   P   N   W   G   K tat gtt ctt ctg tct gcg gga gcg ctc acc gcg ctg atg ttg atc
 Y   V   L   L   S   A   G   A   L   T   A   L   M   L   I
         Rab G transmembrane domain att ttc ctc atg act tgc tgt aga agg gtg aat aga tcc gaa cct
 I   F   L   M   T   C   C   R   R   V   N   R   S   E   P act caa cac aac ctt cga ggc aca ggt cga gaa gta tcc gtc aca
 T   Q   H   N   L   R   G   T   G   R   E   V   S   V   T
Rab G Cterminal cytoplasmatic tails cct caa tct ggc aag att atc tca agt tgg gag tcc cat aag tca
 P   Q   S   G   K   I   I   S   S   W   E   S   H   K   S ggt ggt gag acc cgg ctg AGG TCA ATT GCT ATG ACG TTT CTT GCG
 G   G   E   T   R   L   R   S   I   A   M   T   F   L   A
                             West nile virus TM2 domain GTT GGA GGA GTT TTG CTC TTC CTT TCG GTC AAC GTC CAT GCT GAT
 V   G   G   V   L   L   F   L   S   V   N   V   H   A   D CAA GGA TGC GCC ATC AAC TTT GGC AAG AGA GAG CTC AAG TGC GGA
 Q   G   C   A   I   N   F   G   K   R   E   L   K   C   G
NS1 signal peptide GAT GGT ATC TTC ATA TTT AGA GAC TCT GAT GAC TGG CTG AAC AAG
 D   G   I   F   I   F   R   D   S   D   D   W   L   N   K TAC TCA TAC TAT CCA GAA GAT CCT GTG AAG CTT GCA TCA ATA GTG
 Y   S   Y   Y   P   E   D   P   V   K   L   A   S   I   V AAA GCC TCT TTT GAA GAA GGG AAG TGT GGC CTA AAT TCA GTT GAC
 K   A   S   F   E   E   G   K   C   G   L   N   S   V   D TCC CTT GAG CAT GAG ATG TGG AGA AGC AGG GCA GAT GAG ATC AAT
 S   L   E   H   E   M   W   R   S   R   A   D   E   I   N
```

C terminal part Rabies Glycoprotein G
SEQ ID NO: 10
NQVSGVDLGLPNWGKYVLLSAGALTALMLIIFLMTCCRRVNRSEPTQHNLRGTGREVSV

TPQSGKIISSWESHKSGGETRL

TM Rabies Glycoprotein G
SEQ ID NO: 11
VLLSAGALTALMLIIFLMTCC

Rab cytoplasmatic C terminal
SEQ ID NO: 12
RRVNRSEPTQHNLRGTGREVSVTPQSGKIISSWESHKSGGETRL

WNV TM-2
SEQ ID NO: 13
RSIAMTFLAVGGVLLFLSVNVHA

N terminal part YF NS1
SEQ ID NO: 14
DQGCAINFGKRELKCGDGIFIFRDSDDWLNKYSYYPEDPVKLASIVKASFEEGKCGLNS

VDSLEHEMWRSRADEIN

OVERVIEW OF SEQUENCES DEPICTED IN THE APPLICATION

IIb epitope of Rabies Glycoprotein G
SEQ ID NO: 15
GCTNLSGFS

SEQ ID NO: 16

Glycoprotein G Rabies virus
(ERA strain codon optimized)
SEQ ID NO: 17

```
tggtccctcaagcgctgcttttcgttccctccttgtctttcca
 M  V  P  Q  A  L  L  F  V  P  L  L  V  F  P ctttgttttggaaaatttccaatatacacaattcccgacaaactt
 L  C  F  G  K  F  P  I  Y  T  I  P  D  K  L ggaccctggagtccgatagacattcaccatttgtcttgccctaat
 G  P  W  S  P  I  D  I  H  H  L  S  C  P  N aaccttgtggttgaggacgaggggtgtactaacttgagtgggttc
 N  L  V  V  E  D  E  G  C  T  N  L  S  G  F agttatatggaacttaaggtggggtatatattggctattaaaatg
 S  Y  M  E  L  K  V  G  Y  I  L  A  I  K  M aacgggttcacatgcacaggtgttgtcacggaggcagagacctat
 N  G  F  T  C  T  G  V  V  T  E  A  E  T  Y acaaactttgttgggtacgtaactactacgttcaagaggaaacat
 T  N  F  V  G  Y  V  T  T  T  F  K  R  K  H tttcgcccgactcctgatgcttgtcgcgcggcctataactggaaa
 F  R  P  T  P  D  A  C  R  A  A  Y  N  W  K atggccggggacccacggtacgaggagagcctccacaatccatat
 M  A  G  D  P  R  Y  E  E  S  L  H  N  P  Y cccgactaccggtggctccgcacagtaaagacgactaaggaatct
 P  D  Y  R  W  L  R  T  V  K  T  T  K  E  S ctggttataatatcccctcagtcgccgacctcgatccatatgat
 L  V  I  I  S  P  S  V  A  D  L  D  P  Y  D cggtcacttcatagtcgcgtatttccatccggtaaatgtagtggg
 R  S  L  H  S  R  V  F  P  S  G  K  C  S  G gtagccgtcagtagcacgtactgttccactaatcacgattacact
 V  A  V  S  S  T  Y  C  S  T  N  H  D  Y  T atttggatgccggaaaacccgcggcttgggatgagttgcgatatt
 I  W  M  P  E  N  P  R  L  G  M  S  C  D  I ttcacgaactctcggggaaagcgcgcaagtaagggttctgagacc
 F  T  N  S  R  G  K  R  A  S  K  G  S  E  T tgtggtttcgtggatgaacgaggtctctacaagtcactcaagggt
 C  G  F  V  D  E  R  G  L  Y  K  S  L  K  G gcctgcaagcttaagctttgtggagtactgggactcaggctgatg
 A  C  K  L  K  L  C  G  V  L  G  L  R  L  M gacggcacatgggtggctatgcaaacgtcaaatgaaaccaagtgg
 D  G  T  W  V  A  M  Q  T  S  N  E  T  K  W tgtccgccagatcaactcgtaaatcttcacgattttcgcagtgac
 C  P  P  D  Q  L  V  N  L  H  D  F  R  S  D gagattgaacatcttgtagtcgaagaactcgttagaaagagggaa
 E  I  E  H  L  V  V  E  E  L  V  R  K  R  E gaatgtctcgacgcactcgaatctatcatgactactaaatctgtc
 E  C  L  D  A  L  E  S  I  M  T  T  K  S  V tcatttcgacgcctcagtcacctgagaaaactcgtgccaggattc
 S  F  R  R  L  S  H  L  R  K  L  V  P  G  F
```

| OVERVIEW OF SEQUENCES DEPICTED IN THE APPLICATION |
|---|

```
ggcaaagcttatactatcttcaacaagacgttgatggaagcggac
 G   K   A   Y   T   I   F   N   K   T   L   M   E   A   D gctcattacaaatcagtaagaacttggaatgaaattctgccatcc
 A   H   Y   K   S   V   R   T   W   N   E   I   L   P   S aagggctgccttcgcgtaggagggcgatgccatcctcatgtaaat
 K   G   C   L   R   V   G   G   R   C   H   P   H   V   N ggggtcttctttaacgggataatcttgggacccgacggcaacgta
 G   V   F   F   N   G   I   I   L   G   P   D   G   N   V cttataccagagatgcagagtagtctcctccaacagcacatggag
 L   I   P   E   M   Q   S   S   L   L   Q   Q   H   M   E ttgttggaatccagcgtgatccctctcgttcaccccttggctgat
 L   L   E   S   S   V   I   P   L   V   H   P   L   A   D ccgagcactgtgttcaaagatggagacgaggcggaggatttcgtc
 P   S   T   V   F   K   D   G   D   E   A   E   D   F   V gaagttcacctcccggatgtccataatcaagtttctggagtcgac
 E   V   H   L   P   D   V   H   N   Q   V   S   G   V   D ctcggattgccaaattgggggaagtatgttcttctgtctgcggga
 L   G   L   P   N   W   G   K   Y   V   L   L   S   A   G gcgctcaccgcgctgatgttgatcatttttcctcatgacttgctgt
 A   L   T   A   L   M   L   I   I   F   L   M   T   C   C agaagggtgaatagatccgaacctactcaacacaaccttcgaggc
 R   R   V   N   R   S   E   P   T   Q   H   N   L   R   G acaggtcgagaagtatccgtcacacctcaatctggcaagatttc
 T   G   R   E   V   S   V   T   P   Q   S   G   K   I   I tcaagttgggagtcccataagtcaggtggtgagaccggctg
 S   S   W   E   S   H   K   S   G   G   E   T   R   L
```

Rab G protein sequence
                                                    SEQ ID NO: 17
<u>MVPQALLFVPLLVFPLCFG</u> [signal peptide]

KFPIYTIPDK LGPWSPIDIH HLSCPNNLVV EDE<u>GCTNLSG FS</u>YMELKVGY    50

ILAIKMNGFT CTGVVTEAET YTNFVGYVTT TFKRKHFRPT PDACRAAYNW   100

KMAGDPRYEE SLHNPYPDYR WLRTVKTTKE SLVIISPSVA DLDPYDRSLH   150

SRVFPSGKCS GVAVSSTYCS TNHDYTIWMP ENPRLGMSCD IFTNSRGKRA   200

SKGSETCGFV DERGLYKSLK GACKLKLCGV LGLRLMDGTW VAMQTSNETK   250

WCPPDQLVNL HDFRSDEIEH LVVEELVRKR EECLDALESI MTTKSVSFRR   300

LSHLRKLVPG FGKAYTIFNK TLMEADAHYK SVRTWNEILP SKGCLRVGGR   350

CHPHVNGVFF NGIILGPDGN VLIPEMQSSL LQQHMELLES SVIPLVHPLA   400

DPSTVFKDGD EAEDFVEVHL PDVHNQVSGV DLGLPNWGKY <u>VLLSAGALTA</u>   450

<u>LMLIIFLMTC C</u><u>RRVNRSEPT QHNLRGTGRE VSVTPQSGKI ISSWESHKSG</u>   500

<u>GETRL</u>                                                    505

AA 1-18 of Rabies Glycoprotein G
                                                    SEQ ID NO: 18
MVPQALLFVPLLVFPLCFG TM domain Rabies Glycoprotein G
                                                    SEQ ID NO: 19
VLLSAGALTALMLIIFLMTCC Cytoplasmatic tail RABG
                                                    SEQ ID NO: 20
RRVNRSEPTQHNLRGIGREVSVIPQSGKIISSWESHKSGGETRL

OVERVIEW OF SEQUENCES DEPICTED IN THE APPLICATION

Junction YFV NS1 signal peptide - Rabies
Glycoprotein G
SEQ ID NO: 21

LGVGA DQGCAINFG KFPIY

Junction WNV TM2- NS1 signal sequence-YFV
SEQ ID NO: 22

VNVHA DQGCAINFG KRELK

The invention claimed is:

1. A polynucleotide comprising a sequence of a live, infectious, attenuated Flavivirus wherein a nucleotide sequence encoding at least a part of a Lyssavirus G protein sequence is located at the intergenic region between an E gene and an NS1 gene of the Flavivirus, such that a chimeric virus is expressed, wherein the encoded sequence is located C terminally of an E protein of the Flavivirus and N terminally of a signal peptide of an NS1 protein of the Flavivirus, and wherein the encoded sequence comprises in the following order:
   (1) a further signal peptide of a Flavivirus NS1 protein,
   (2) a lyssavirus G protein lacking a functional signal peptide, comprising an IIb epitope, comprising a C terminal TM membrane, and comprising a C terminal cytoplasmatic sequence, and
   (3) a TM2 domain of a flaviviral E protein.

2. The polynucleotide according to claim 1, wherein the sequence of the live, infectious, attenuated Flavivirus is Yellow Fever virus.

3. The polynucleotide according to claim 1, wherein the Lyssavirus is Rabies virus.

4. The polynucleotide according to claim 1, wherein the Lyssavirus G protein is an ERA strain Rabies G protein.

5. The polynucleotide according to claim 1, wherein the signal peptide of the NS1 protein comprises SEQ ID NO:6.

6. The polynucleotide according to claim 1, wherein the IIb epitope comprises SEQ ID NO:15.

7. The polynucleotide according to claim 1, wherein the TM2 domain of the flaviviral E protein is from West Nile virus.

8. The polynucleotide according to claim 1, wherein the TM2 domain of the flaviviral E protein has SEQ ID NO:13.

9. The polynucleotide according to claim 4, wherein the signal peptide of the Rabies G protein comprises a F14S mutation that renders the signal peptide non-functional.

10. The polynucleotide according to claim 4, wherein the Rabies G protein lacks the N terminal signal sequence consisting of SEQ ID NO:18.

11. The polynucleotide according to claim 3, wherein, at the junction of Flavivirus E gene, NS1 signal peptide, and Rabies G protein, the sequence of the chimeric virus comprises SEQ ID NO:21.

12. The polynucleotide according to claim 7, wherein the live, infectious, attenuated Flavivirus is Yellow Fever virus and wherein at the junction of the West Nile virus TM2 domain and the NS1 signal sequence of the Yellow Fever virus, the sequence of the chimeric virus comprises SEQ ID NO:22.

13. The polynucleotide according to claim 1, wherein the encoded sequence of the chimeric virus comprises SEQ ID NO:2 or a sequence having at least 95% sequence identity therewith.

14. The polynucleotide according to claim 1, wherein the polynucleotide comprises SEQ ID NO: 1 or a sequence having at least 95% sequence identity therewith.

15. A chimeric live, infectious, attenuated Flavivirus, wherein at least a part of a Lyssavirus G protein is located between an E protein and a NS1 protein of the Flavivirus, such that C terminally of the E protein and N terminally of a signal peptide of the NS1 protein the virus comprises in the following order:
   (1) a further signal peptide of a Flavivirus NS1 protein,
   (2) a lyssavirus G protein lacking a functional signal peptide, and comprising an IIb epitope, comprising a C terminal TM membrane and a C terminal cytoplasmatic sequence, and
   (3) a TM2 domain of a flaviviral E protein.

16. The chimeric live, infectious, attenuated Flavivirus according to claim 15, wherein the Flavivirus of the live, infectious, attenuated Flavivirus is Yellow Fever virus and/or wherein the lyssavirus is Rabies virus.

17. A method of vaccinating an individual, the method comprising:
administering a chimeric live, infectious, attenuated Flavivirus, wherein at least a part of a Lyssavirus G protein is located between an E protein and a NS1 protein of the Flavivirus, such that C terminally of the E protein and N terminally of a signal peptide of the NS1 protein the virus comprises in the following order:
(1) a further signal peptide of a Flavivirus NS1 protein,
(2) a lyssavirus G protein lacking a functional signal peptide, and comprising an IIb epitope, comprising a C terminal TM membrane and a C terminal cytoplasmatic sequence, and
(3) a TM2 domain of a flaviviral E protein.

18. The method of vaccinating according to claim 17, which is a vaccination for a lyssavirus.

19. The method of vaccinating according to claim 17, which is a simultaneous vaccination for a lyssavirus and a flavivirus.

20. The method of vaccination according to claim 17, wherein the lyssavirus is Rabies virus and the flavivirus is Yellow Fever virus.

21. A method of preparing a vaccine against a lyssavirus infection, the method comprising:
(a) providing a BAC, the BAC comprising:
an inducible bacterial ori sequence for amplification of the BAC to more than 10 copies per bacterial cell, and
a viral expression cassette comprising a cDNA of a Flavivirus lyssavirus chimeric virus according to claim 1, and comprising cis-regulatory elements for transcription of the viral cDNA in mammalian cells and for processing of RNA transcribed from the viral cDNA into an infectious RNA virus;
(b) transfecting mammalian cells with the BAC of (a) and passaging the transfected mammalian cells;
(c) validating replicated virus of the transfected cells of (b) for virulence and capacity of generating antibodies and inducing protection against lyssavirus infection;
(d) cloning the virus validated in (c) into a vector; and
(e) formulating the vector into a vaccine formulation.

22. The method according to claim 21, wherein the Flavivirus is Yellow Fever virus.

23. The method according to claim 21, wherein the lyssavirus is Rabies virus.

* * * * *

SEQUENCE LISTING

<160> NUMBER OF SEQ ID NOS: 22

<210> SEQ ID NO 1
<211> LENGTH: 441
<212> TYPE: DNA
<213> ORGANISM: Artificial Sequence
<220> FEATURE:
<223> OTHER INFORMATION: fragment YFV - Rab G chimeric construct
<220> FEATURE:
<221> NAME/KEY: CDS
<222> LOCATION: (1)..(441)

<400> SEQUENCE: 1

```
gga aag ttg ttc act cag acc atg aaa ggc gtg gaa cgc ctg gcc gtc      48
Gly Lys Leu Phe Thr Gln Thr Met Lys Gly Val Glu Arg Leu Ala Val
1               5                   10                  15 atg gga gac acc gcc tgg gat ttc agc tcc gct gga ggg ttc ttc act      96
Met Gly Asp Thr Ala Trp Asp Phe Ser Ser Ala Gly Gly Phe Phe Thr
            20                  25                  30 tcg gtt ggg aaa gga att cat acg gtg ttt ggc tct gcc ttt cag ggg     144
Ser Val Gly Lys Gly Ile His Thr Val Phe Gly Ser Ala Phe Gln Gly
        35                  40                  45 cta ttt ggc ggc ttg aac tgg ata aca aag gtc atc atg ggg gcg gta     192
Leu Phe Gly Gly Leu Asn Trp Ile Thr Lys Val Ile Met Gly Ala Val
    50                  55                  60 ctt ata tgg gtt ggc atc aac aca aga aac atg aca atg tcc atg agc     240
Leu Ile Trp Val Gly Ile Asn Thr Arg Asn Met Thr Met Ser Met Ser
65                  70                  75                  80 atg atc ttg gta gga gtg atc atg atg ttt ttg tct cta gga gtt ggc     288
Met Ile Leu Val Gly Val Ile Met Met Phe Leu Ser Leu Gly Val Gly
                85                  90                  95 gcc gac cag ggc tgc gcg ata aat ttc ggt aaa ttt cca ata tac aca     336
Ala Asp Gln Gly Cys Ala Ile Asn Phe Gly Lys Phe Pro Ile Tyr Thr
            100                 105                 110 att ccc gac aaa ctt gga ccc tgg agt ccg ata gac att cac cat ttg     384
Ile Pro Asp Lys Leu Gly Pro Trp Ser Pro Ile Asp Ile His His Leu
        115                 120                 125 tct tgc cct aat aac ctt gtg gtt gag gac gag ggg tgt act aac ttg     432
Ser Cys Pro Asn Asn Leu Val Val Glu Asp Glu Gly Cys Thr Asn Leu
    130                 135                 140 agt ggg ttc                                                          441
Ser Gly Phe
145
```

<210> SEQ ID NO 2
<211> LENGTH: 147
<212> TYPE: PRT
<213> ORGANISM: Artificial Sequence
<220> FEATURE:
<223> OTHER INFORMATION: Synthetic Construct

<400> SEQUENCE: 2

```
Gly Lys Leu Phe Thr Gln Thr Met Lys Gly Val Glu Arg Leu Ala Val
1               5                   10                  15

Met Gly Asp Thr Ala Trp Asp Phe Ser Ser Ala Gly Gly Phe Phe Thr
            20                  25                  30

Ser Val Gly Lys Gly Ile His Thr Val Phe Gly Ser Ala Phe Gln Gly
        35                  40                  45

Leu Phe Gly Gly Leu Asn Trp Ile Thr Lys Val Ile Met Gly Ala Val
    50                  55                  60

Leu Ile Trp Val Gly Ile Asn Thr Arg Asn Met Thr Met Ser Met Ser
65                  70                  75                  80

Met Ile Leu Val Gly Val Ile Met Met Phe Leu Ser Leu Gly Val Gly
                85                  90                  95

Ala Asp Gln Gly Cys Ala Ile Asn Phe Gly Lys Phe Pro Ile Tyr Thr
            100                 105                 110

Ile Pro Asp Lys Leu Gly Pro Trp Ser Pro Ile Asp Ile His His Leu
            115                 120                 125

Ser Cys Pro Asn Asn Leu Val Val Glu Asp Glu Gly Cys Thr Asn Leu
130                 135                 140

Ser Gly Phe
145
```

<210> SEQ ID NO 3
<211> LENGTH: 93
<212> TYPE: PRT
<213> ORGANISM: Artificial Sequence
<220> FEATURE:
<223> OTHER INFORMATION: C terminal part of YF-E protein

<400> SEQUENCE: 3

```
Gly Lys Leu Phe Thr Gln Thr Met Lys Gly Val Glu Arg Leu Ala Val
1               5                   10                  15

Met Gly Asp Thr Ala Trp Asp Phe Ser Ser Ala Gly Gly Phe Phe Thr
            20                  25                  30

Ser Val Gly Lys Gly Ile His Thr Val Phe Gly Ser Ala Phe Gln Gly
        35                  40                  45

Leu Phe Gly Gly Leu Asn Trp Ile Thr Lys Val Ile Met Gly Ala Val
    50                  55                  60

Leu Ile Trp Val Gly Ile Asn Thr Arg Asn Met Thr Met Ser Met Ser
65                  70                  75                  80

Met Ile Leu Val Gly Val Ile Met Met Phe Leu Ser Leu
                85                  90
```

<210> SEQ ID NO 4
<211> LENGTH: 22
<212> TYPE: PRT
<213> ORGANISM: Artificial Sequence
<220> FEATURE:
<223> OTHER INFORMATION: YFE-TM1

<400> SEQUENCE: 4

```
Gly Gly Leu Asn Trp Ile Thr Lys Val Ile Met Gly Ala Val Leu Ile
1               5                   10                  15

Trp Val Gly Ile Asn Thr
            20
```

<210> SEQ ID NO 5

-continued

```
<211> LENGTH: 23
<212> TYPE: PRT
<213> ORGANISM: Artificial Sequence
<220> FEATURE:
<223> OTHER INFORMATION: YFE-TM2

<400> SEQUENCE: 5

Met Thr Met Ser Met Ser Met Ile Leu Val Gly Val Ile Met Met Phe
1               5                   10                  15

Leu Ser Leu Gly Val Gly Ala
            20

<210> SEQ ID NO 6
<211> LENGTH: 9
<212> TYPE: PRT
<213> ORGANISM: Artificial Sequence
<220> FEATURE:
<223> OTHER INFORMATION: NS1 N terminal 9 AA

<400> SEQUENCE: 6

Asp Gln Gly Cys Ala Ile Asn Phe Gly
1               5

<210> SEQ ID NO 7
<211> LENGTH: 41
<212> TYPE: PRT
<213> ORGANISM: Rabies virus

<400> SEQUENCE: 7

Lys Phe Pro Ile Tyr Thr Ile Pro Asp Lys Leu Gly Pro Trp Ser Pro
1               5                   10                  15

Ile Asp Ile His His Leu Ser Cys Pro Asn Asn Leu Val Val Glu Asp
            20                  25                  30

Glu Gly Cys Thr Asn Leu Ser Gly Phe
        35                  40

<210> SEQ ID NO 8
<211> LENGTH: 540
<212> TYPE: DNA
<213> ORGANISM: Artificial Sequence
<220> FEATURE:
<223> OTHER INFORMATION: fragment YFV - Rab G chimeric construct
<220> FEATURE:
<221> NAME/KEY: CDS
<222> LOCATION: (1)..(540)

<400> SEQUENCE: 8 aat caa gtt tct gga gtc gac ctc gga ttg cca aat tgg ggg aag tat      48
Asn Gln Val Ser Gly Val Asp Leu Gly Leu Pro Asn Trp Gly Lys Tyr
1               5                   10                  15 gtt ctt ctg tct gcg gga gcg ctc acc gcg ctg atg ttg atc att ttc      96
Val Leu Leu Ser Ala Gly Ala Leu Thr Ala Leu Met Leu Ile Ile Phe
            20                  25                  30 ctc atg act tgc tgt aga agg gtg aat aga tcc gaa cct act caa cac     144
Leu Met Thr Cys Cys Arg Arg Val Asn Arg Ser Glu Pro Thr Gln His
        35                  40                  45 aac ctt cga ggc aca ggt cga gaa gta tcc gtc aca cct caa tct ggc     192
Asn Leu Arg Gly Thr Gly Arg Glu Val Ser Val Thr Pro Gln Ser Gly
    50                  55                  60 aag att atc tca agt tgg gag tcc cat aag tca ggt ggt gag acc cgg     240
Lys Ile Ile Ser Ser Trp Glu Ser His Lys Ser Gly Gly Glu Thr Arg
65                  70                  75                  80
```

```
ctg agg tca att gct atg acg ttt ctt gcg gtt gga gga gtt ttg ctc       288
Leu Arg Ser Ile Ala Met Thr Phe Leu Ala Val Gly Gly Val Leu Leu
            85                  90                  95 ttc ctt tcg gtc aac gtc cat gct gat caa gga tgc gcc atc aac ttt       336
Phe Leu Ser Val Asn Val His Ala Asp Gln Gly Cys Ala Ile Asn Phe
                100                 105                 110 ggc aag aga gag ctc aag tgc gga gat ggt atc ttc ata ttt aga gac       384
Gly Lys Arg Glu Leu Lys Cys Gly Asp Gly Ile Phe Ile Phe Arg Asp
            115                 120                 125 tct gat gac tgg ctg aac aag tac tca tac tat cca gaa gat cct gtg       432
Ser Asp Asp Trp Leu Asn Lys Tyr Ser Tyr Tyr Pro Glu Asp Pro Val
    130                 135                 140 aag ctt gca tca ata gtg aaa gcc tct ttt gaa gaa ggg aag tgt ggc       480
Lys Leu Ala Ser Ile Val Lys Ala Ser Phe Glu Glu Gly Lys Cys Gly
145                 150                 155                 160 cta aat tca gtt gac tcc ctt gag cat gag atg tgg aga agc agg gca       528
Leu Asn Ser Val Asp Ser Leu Glu His Glu Met Trp Arg Ser Arg Ala
                165                 170                 175 gat gag atc aat                                                       540
Asp Glu Ile Asn
            180

<210> SEQ ID NO 9
<211> LENGTH: 180
<212> TYPE: PRT
<213> ORGANISM: Artificial Sequence
<220> FEATURE:
<223> OTHER INFORMATION: Synthetic Construct

<400> SEQUENCE: 9

Asn Gln Val Ser Gly Val Asp Leu Gly Leu Pro Asn Trp Gly Lys Tyr
1               5                   10                  15

Val Leu Leu Ser Ala Gly Ala Leu Thr Ala Leu Met Leu Ile Ile Phe
                20                  25                  30

Leu Met Thr Cys Cys Arg Arg Val Asn Arg Ser Glu Pro Thr Gln His
            35                  40                  45

Asn Leu Arg Gly Thr Gly Arg Glu Val Ser Val Thr Pro Gln Ser Gly
    50                  55                  60

Lys Ile Ile Ser Ser Trp Glu Ser His Lys Ser Gly Gly Glu Thr Arg
65                  70                  75                  80

Leu Arg Ser Ile Ala Met Thr Phe Leu Ala Val Gly Gly Val Leu Leu
                85                  90                  95

Phe Leu Ser Val Asn Val His Ala Asp Gln Gly Cys Ala Ile Asn Phe
            100                 105                 110

Gly Lys Arg Glu Leu Lys Cys Gly Asp Gly Ile Phe Ile Phe Arg Asp
        115                 120                 125

Ser Asp Asp Trp Leu Asn Lys Tyr Ser Tyr Tyr Pro Glu Asp Pro Val
    130                 135                 140

Lys Leu Ala Ser Ile Val Lys Ala Ser Phe Glu Glu Gly Lys Cys Gly
145                 150                 155                 160

Leu Asn Ser Val Asp Ser Leu Glu His Glu Met Trp Arg Ser Arg Ala
                165                 170                 175

Asp Glu Ile Asn
            180

<210> SEQ ID NO 10
<211> LENGTH: 81
<212> TYPE: PRT
```

```
<213> ORGANISM: Rabies virus

<400> SEQUENCE: 10

Asn Gln Val Ser Gly Val Asp Leu Gly Leu Pro Asn Trp Gly Lys Tyr
1               5                   10                  15

Val Leu Leu Ser Ala Gly Ala Leu Thr Ala Leu Met Leu Ile Ile Phe
                20                  25                  30

Leu Met Thr Cys Cys Arg Arg Val Asn Arg Ser Glu Pro Thr Gln His
            35                  40                  45

Asn Leu Arg Gly Thr Gly Arg Glu Val Ser Val Thr Pro Gln Ser Gly
        50                  55                  60

Lys Ile Ile Ser Ser Trp Glu Ser His Lys Ser Gly Gly Glu Thr Arg
65                  70                  75                  80

Leu

<210> SEQ ID NO 11
<211> LENGTH: 21
<212> TYPE: PRT
<213> ORGANISM: Rabies virus

<400> SEQUENCE: 11

Val Leu Leu Ser Ala Gly Ala Leu Thr Ala Leu Met Leu Ile Ile Phe
1               5                   10                  15

Leu Met Thr Cys Cys
            20

<210> SEQ ID NO 12
<211> LENGTH: 44
<212> TYPE: PRT
<213> ORGANISM: Rabies virus

<400> SEQUENCE: 12

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
                20                  25                  30

Trp Glu Ser His Lys Ser Gly Gly Glu Thr Arg Leu
            35                  40

<210> SEQ ID NO 13
<211> LENGTH: 23
<212> TYPE: PRT
<213> ORGANISM: West Nile virus

<400> SEQUENCE: 13

Arg Ser Ile Ala Met Thr Phe Leu Ala Val Gly Gly Val Leu Leu Phe
1               5                   10                  15

Leu Ser Val Asn Val His Ala
                20

<210> SEQ ID NO 14
<211> LENGTH: 76
<212> TYPE: PRT
<213> ORGANISM: Yellow fever virus

<400> SEQUENCE: 14

Asp Gln Gly Cys Ala Ile Asn Phe Gly Lys Arg Glu Leu Lys Cys Gly
1               5                   10                  15

Asp Gly Ile Phe Ile Phe Arg Asp Ser Asp Asp Trp Leu Asn Lys Tyr
                20                  25                  30
```

```
Ser Tyr Tyr Pro Glu Asp Pro Val Lys Leu Ala Ser Ile Val Lys Ala
         35                  40                  45

Ser Phe Glu Glu Gly Lys Cys Gly Leu Asn Ser Val Asp Ser Leu Glu
 50                  55                  60

His Glu Met Trp Arg Ser Arg Ala Asp Glu Ile Asn
 65                  70                  75

<210> SEQ ID NO 15
<211> LENGTH: 9
<212> TYPE: PRT
<213> ORGANISM: Rabies virus

<400> SEQUENCE: 15

Gly Cys Thr Asn Leu Ser Gly Phe Ser
 1               5

<210> SEQ ID NO 16
<211> LENGTH: 1572
<212> TYPE: DNA
<213> ORGANISM: Rabies virus
<220> FEATURE:
<221> NAME/KEY: CDS
<222> LOCATION: (1)..(1572)

<400> SEQUENCE: 16 atg gtc cct caa gcg ctg ctt ttc gtt ccc ctc ctt gtc ttt cca ctt      48
Met Val Pro Gln Ala Leu Leu Phe Val Pro Leu Leu Val Phe Pro Leu
 1               5                  10                  15 tgt ttt gga aaa ttt cca ata tac aca att ccc gac aaa ctt gga ccc      96
Cys Phe Gly Lys Phe Pro Ile Tyr Thr Ile Pro Asp Lys Leu Gly Pro
             20                  25                  30 tgg agt ccg ata gac att cac cat ttg tct tgc cct aat aac ctt gtg     144
Trp Ser Pro Ile Asp Ile His His Leu Ser Cys Pro Asn Asn Leu Val
         35                  40                  45 gtt gag gac gag ggg tgt act aac ttg agt ggg ttc agt tat atg gaa     192
Val Glu Asp Glu Gly Cys Thr Asn Leu Ser Gly Phe Ser Tyr Met Glu
 50                  55                  60 ctt aag gtg ggg tat ata ttg gct att aaa atg aac ggg ttc aca tgc     240
Leu Lys Val Gly Tyr Ile Leu Ala Ile Lys Met Asn Gly Phe Thr Cys
 65                  70                  75                  80 aca ggt gtt gtc acg gag gca gag acc tat aca aac ttt gtt ggg tac     288
Thr Gly Val Val Thr Glu Ala Glu Thr Tyr Thr Asn Phe Val Gly Tyr
                 85                  90                  95 gta act act acg ttc aag agg aaa cat ttt cgc ccg act cct gat gct     336
Val Thr Thr Thr Phe Lys Arg Lys His Phe Arg Pro Thr Pro Asp Ala
            100                 105                 110 tgt cgc gcg gcc tat aac tgg aaa atg gcc ggg gac cca cgg tac gag     384
Cys Arg Ala Ala Tyr Asn Trp Lys Met Ala Gly Asp Pro Arg Tyr Glu
        115                 120                 125 gag agc ctc cac aat cca tat ccc gac tac cgg tgg ctc cgc aca gta     432
Glu Ser Leu His Asn Pro Tyr Pro Asp Tyr Arg Trp Leu Arg Thr Val
    130                 135                 140 aag acg act aag gaa tct ctg gtt ata ata tcc ccc tca gtc gcc gac     480
Lys Thr Thr Lys Glu Ser Leu Val Ile Ile Ser Pro Ser Val Ala Asp
145                 150                 155                 160 ctc gat cca tat gat cgg tca ctt cat agt cgc gta ttt cca tcc ggt     528
Leu Asp Pro Tyr Asp Arg Ser Leu His Ser Arg Val Phe Pro Ser Gly
                165                 170                 175 aaa tgt agt ggg gta gcc gtc agt agc acg tac tgt tcc act aat cac     576
Lys Cys Ser Gly Val Ala Val Ser Ser Thr Tyr Cys Ser Thr Asn His
            180                 185                 190
```

-continued

```
gat tac act att tgg atg ccg gaa aac ccg cgg ctt ggg atg agt tgc    624
Asp Tyr Thr Ile Trp Met Pro Glu Asn Pro Arg Leu Gly Met Ser Cys
        195                 200                 205 gat att ttc acg aac tct cgg gga aag cgc gca agt aag ggt tct gag    672
Asp Ile Phe Thr Asn Ser Arg Gly Lys Arg Ala Ser Lys Gly Ser Glu
    210                 215                 220 acc tgt ggt ttc gtg gat gaa cga ggt ctc tac aag tca ctc aag ggt    720
Thr Cys Gly Phe Val Asp Glu Arg Gly Leu Tyr Lys Ser Leu Lys Gly
225                 230                 235                 240 gcc tgc aag ctt aag ctt tgt gga gta ctg gga ctc agg ctg atg gac    768
Ala Cys Lys Leu Lys Leu Cys Gly Val Leu Gly Leu Arg Leu Met Asp
                245                 250                 255 ggc aca tgg gtg gct atg caa acg tca aat gaa acc aag tgg tgt ccg    816
Gly Thr Trp Val Ala Met Gln Thr Ser Asn Glu Thr Lys Trp Cys Pro
            260                 265                 270 cca gat caa ctc gta aat ctt cac gat ttt cgc agt gac gag att gaa    864
Pro Asp Gln Leu Val Asn Leu His Asp Phe Arg Ser Asp Glu Ile Glu
        275                 280                 285 cat ctt gta gtc gaa gaa ctc gtt aga aag agg gaa gaa tgt ctc gac    912
His Leu Val Val Glu Glu Leu Val Arg Lys Arg Glu Glu Cys Leu Asp
    290                 295                 300 gca ctc gaa tct atc atg act act aaa tct gtc tca ttt cga cgc ctc    960
Ala Leu Glu Ser Ile Met Thr Thr Lys Ser Val Ser Phe Arg Arg Leu
305                 310                 315                 320 agt cac ctg aga aaa ctc gtg cca gga ttc ggc aaa gct tat act atc   1008
Ser His Leu Arg Lys Leu Val Pro Gly Phe Gly Lys Ala Tyr Thr Ile
                325                 330                 335 ttc aac aag acg ttg atg gaa gcg gac gct cat tac aaa tca gta aga   1056
Phe Asn Lys Thr Leu Met Glu Ala Asp Ala His Tyr Lys Ser Val Arg
        340                 345                 350 act tgg aat gaa att ctg cca tcc aag ggc tgc ctt cgc gta gga ggg   1104
Thr Trp Asn Glu Ile Leu Pro Ser Lys Gly Cys Leu Arg Val Gly Gly
    355                 360                 365 cga tgc cat cct cat gta aat ggg gtc ttc ttt aac ggg ata atc ttg   1152
Arg Cys His Pro His Val Asn Gly Val Phe Phe Asn Gly Ile Ile Leu
370                 375                 380 gga ccc gac ggc aac gta ctt ata cca gag atg cag agt agt ctc ctc   1200
Gly Pro Asp Gly Asn Val Leu Ile Pro Glu Met Gln Ser Ser Leu Leu
385                 390                 395                 400 caa cag cac atg gag ttg ttg gaa tcc agc gtg atc cct ctc gtt cac   1248
Gln Gln His Met Glu Leu Leu Glu Ser Ser Val Ile Pro Leu Val His
                405                 410                 415 ccc ttg gct gat ccg agc act gtg ttc aaa gat gga gac gag gcg gag   1296
Pro Leu Ala Asp Pro Ser Thr Val Phe Lys Asp Gly Asp Glu Ala Glu
        420                 425                 430 gat ttc gtc gaa gtt cac ctc ccg gat gtc cat aat caa gtt tct gga   1344
Asp Phe Val Glu Val His Leu Pro Asp Val His Asn Gln Val Ser Gly
    435                 440                 445 gtc gac ctc gga ttg cca aat tgg ggg aag tat gtt ctt ctg tct gcg   1392
Val Asp Leu Gly Leu Pro Asn Trp Gly Lys Tyr Val Leu Leu Ser Ala
450                 455                 460 gga gcg ctc acc gcg ctg atg ttg atc att ttc ctc atg act tgc tgt   1440
Gly Ala Leu Thr Ala Leu Met Leu Ile Ile Phe Leu Met Thr Cys Cys
465                 470                 475                 480 aga agg gtg aat aga tcc gaa cct act caa cac aac ctt cga ggc aca   1488
Arg Arg Val Asn Arg Ser Glu Pro Thr Gln His Asn Leu Arg Gly Thr
                485                 490                 495
```

```
ggt cga gaa gta tcc gtc aca cct caa tct ggc aag att atc tca agt     1536
Gly Arg Glu Val Ser Val Thr Pro Gln Ser Gly Lys Ile Ile Ser Ser
        500             505                 510 tgg gag tcc cat aag tca ggt ggt gag acc cgg ctg                     1572
Trp Glu Ser His Lys Ser Gly Gly Glu Thr Arg Leu
        515             520
```

<210> SEQ ID NO 17
<211> LENGTH: 524
<212> TYPE: PRT
<213> ORGANISM: Rabies virus

<400> SEQUENCE: 17

```
Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr Arg Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335
```

-continued

```
Phe Asn Lys Thr Leu Met Glu Ala Asp Ala His Tyr Lys Ser Val Arg
                340                 345                 350

Thr Trp Asn Glu Ile Leu Pro Ser Lys Gly Cys Leu Arg Val Gly Gly
            355                 360                 365

Arg Cys His Pro His Val Asn Gly Val Phe Phe Asn Gly Ile Ile Leu
        370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520

<210> SEQ ID NO 18
<211> LENGTH: 19
<212> TYPE: PRT
<213> ORGANISM: Rabies virus

<400> SEQUENCE: 18

Met Val Pro Gln Ala Leu Leu Phe Val Pro Leu Leu Val Phe Pro Leu
1               5                   10                  15

Cys Phe Gly

<210> SEQ ID NO 19
<211> LENGTH: 21
<212> TYPE: PRT
<213> ORGANISM: Rabies virus

<400> SEQUENCE: 19

Val Leu Leu Ser Ala Gly Ala Leu Thr Ala Leu Met Leu Ile Ile Phe
1               5                   10                  15

Leu Met Thr Cys Cys
            20

<210> SEQ ID NO 20
<211> LENGTH: 44
<212> TYPE: PRT
<213> ORGANISM: Rabies virus

<400> SEQUENCE: 20

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30
```

```
Trp Glu Ser His Lys Ser Gly Gly Glu Thr Arg Leu
        35                  40

<210> SEQ ID NO 21
<211> LENGTH: 19
<212> TYPE: PRT
<213> ORGANISM: Artificial Sequence
<220> FEATURE:
<223> OTHER INFORMATION: Junction YFV NS1 signal peptide - Rabies
      Glycoprotein G

<400> SEQUENCE: 21

Leu Gly Val Gly Ala Asp Gln Gly Cys Ala Ile Asn Phe Gly Lys Phe
1               5                   10                  15

Pro Ile Tyr

<210> SEQ ID NO 22
<211> LENGTH: 19
<212> TYPE: PRT
<213> ORGANISM: Artificial Sequence
<220> FEATURE:
<223> OTHER INFORMATION: Junction WNV TM2- NS1 signal sequence-YFV

<400> SEQUENCE: 22

Val Asn Val His Ala Asp Gln Gly Cys Ala Ile Asn Phe Gly Lys Arg
1               5                   10                  15

Glu Leu Lys
```